United States Patent
Cai et al.

(10) Patent No.: US 7,176,234 B2
(45) Date of Patent: **\*Feb. 13, 2007**

(54) DERIVATIVES OF GAMBOGIC ACID AND ANALOGS AS ACTIVATORS OF CASPASES AND INDUCERS OF APOPTOSIS

(75) Inventors: Sui Xiong Cai, San Diego, CA (US); Shailaja Kasibhatla, San Diego, CA (US); Kristin P. Ollis, San Diego, CA (US); Han-Zhong Zhang, San Diego, CA (US); John A. Drewe, Carlsbad, CA (US); Ben Tseng, San Diego, CA (US); Nilantha Sudath Sirisoma, San Diego, CA (US)

(73) Assignee: Cytovia, Inc., San Diego, CA (US)

( * ) Notice: Subject to any disclaimer, the term of this patent is extended or adjusted under 35 U.S.C. 154(b) by 106 days.

This patent is subject to a terminal disclaimer.

(21) Appl. No.: 10/609,670

(22) Filed: Jul. 1, 2003

(65) Prior Publication Data

US 2004/0082066 A1 Apr. 29, 2004

Related U.S. Application Data

(60) Provisional application No. 60/413,649, filed on Sep. 26, 2002, provisional application No. 60/392,358, filed on Jul. 1, 2002.

(51) Int. Cl.
*A61K 31/352* (2006.01)
*C07D 313/06* (2006.01)
(52) U.S. Cl. ...................... 514/450; 549/268
(58) Field of Classification Search ............... 514/450; 549/268
See application file for complete search history.

(56) References Cited

U.S. PATENT DOCUMENTS 6,462,041 B1 10/2002 Cai et al.
6,613,762 B2 9/2003 Cai et al.

FOREIGN PATENT DOCUMENTS

WO WO 00/44216 A2 8/2000
WO WO 00/45165 A1 8/2000

OTHER PUBLICATIONS

Wiseman, L.R. and Spencer, C.M., "Paclitaxel—An Update of its Use in the Treatment of Metastatic Breast Cancer and Ovarian and Other Gynaecological Cancers," *Drugs & Aging* 12:305-334, Adis International Limited (1998).

Written Opinion for International Patent Application No. PCT/US03/20668, 5 pages, mailed Jan. 23, 2006.

Adawadkar, P.D., et al., "Colouring Matters of *Garcinia morella*: Part VIII—Morellinol, Dihydromorelloflavone & Morelloflavone-7"-β-glucoside", *Indian J. Chem.* 14B:19-21, The Council of Scientific & Industrial Research, New Delhi (1976).

Adjei, A.A., et al., "Synergy of the Protein Farnesyltransferase Inhibitor SCH66336 and Cisplatin in Human Cancer Cell Lines," *Clin. Cancer Res.* 7:1438-1445, American Association for Cancer Research (May 2001).

Ahmad, S.A., et al., "Gamboge. Part II," *J. Chem. Soc.* (C)1:772-779, The Chemical Society (1966).

Almond, J. B., and Cohen, G.M., "The proteasome: a novel target for cancer chemotherapy," *Leukemia* 16:433-443, Nature Publishing Group (Apr. 2002).

Asano, J., et al., "Cytotoxic Xanthones for *Garcinia hanbury I*," *Phytochemistry* 41:815-820, Elsevier Science, Ltd. (1996).

Batteux, F., et al., "Gene Therapy of Experimental Autoimmune Thyroiditis by In Vivo Administration of Plasmid DNA Coding for Fas Ligand," *J. Immunol.* 162:603-608, The American Association of Immunologists (1999).

Benning, C.M., and Kyprianou, N., "Quinazoline-derived α1-Adrenoceptor Antagonists Induce Prostate Cancer Cell Apoptosis Via an α1-Adrenoreceptor-independent Action," *Cancer Res.* 62:597-602, American Association for Cancer Research (Jan. 2002).

Bhat, H.B., et al., "The Colouring Matters of *Garcinia morella*: Part V—Isolation of Desoxymorellin & Dihydroisomorallin," *Indian J. Chem.* 2:405-410, The Council of Scientific & Industrial Research, New Delhi (1964).

(Continued)

*Primary Examiner*—Taofiq Solola
(74) *Attorney, Agent, or Firm*—Sterne, Kessler, Goldstein & Fox P.L.L.C.

(57) ABSTRACT

The present invention is directed to derivatives of gambogic acid and analogs thereof. Exemplary gambogic acid derivatives of the present invention include, among others, derivatives substituted in the C10 and C28 positions of gambogic acid. The present invention also relates to the discovery that certain preferred compounds of the present invention are activators of caspases and inducers of apoptosis. Therefore, the activators of caspases and inducers of apoptosis of this invention can be used to induce cell death in a variety of clinical conditions in which uncontrolled growth and spread of abnormal cells occurs.

45 Claims, No Drawings

OTHER PUBLICATIONS

Blanke, C.D., "Celecoxib With Chemotherapy in Colorectal Cancer," *Oncology* 16(Suppl. 3):17-21, CMP Healthcare Media Publishing Group (Apr. 2002).
Boirivant, M., et al., "Lamina Propia T Cells in Crohn's Disease and Other Gastrointestinal Inflammation Show Defective CD2 Pathway-Induced Apoptosis," *Gastroenterology* 116:557-565, W.B. Saunders Co. (1999).
Calabresi, P., and Chabner, B.A., "Chemotherapy of Neoplastic Diseases: Introduction," in *Goodman & Gilman's The Pharmacological Basis of Therapeutics*, Section X, Chapter 51, 9th ed., Wonsiewicz, M.J., and McCurdy, P., eds., McGraw-Hill Health Professions Division, New York, NY, pp. 1225-1287 (1996).
Cao, S-G., et al., "Cytotoxic Caged Tetraprenylated Xanthonoids from *Garcinia gaudichaudii* (Guttiferae)," *Tetrahedron Lett.* 39:3353-3356, Elsevier Science, Ltd. (1998).
Cao, S-G., et al., "Novel Cytotoxic Polyprenylated Xanthonoids from *Garcinia gaudichaudii* (Guttiferae)," *Tetrahedron* 54:10915-10924, Elsevier Science, Ltd. (1998).
Chinnaiyan, A.M., et al., "The inhibition of pro-apoptotic ICE-like proteases enhances HIV replication," *Nat. Med.* 3:333-337, Nature Publishing Company (1997).
Coven, T.R., et al., "PUVA-induced lymphocyte apoptosis: Mechanism of action in psoriasis," *Photodermatol. Photoimmunol. Photomed.* 15:22-27, Blackwell Publishing (1999).
Delgado, C., et al., "The Uses and Properties of PEG-Linked Proteins," *Crit. Rev. Ther. Drug Carrier Syst.* 9:249-304, CRC Press, Inc. (1992).
Friesen, C., et al., "Involvement of the CD95 (APO-1/Fas) receptor/ligand system in drug-induced apoptosis in leukemia cells," *Nat. Med.* 2:574-577, Nature Publishing Company (1996).
Giermasz, A., et al., "Potentiating Antitumor Effects of a Combination Therapy with Lovastatin and Butyrate in the Lewis Lung Carcinoma Model in Mice," *Int. J. Cancer* 97:746-750, Wiley-Liss, Inc. (Feb. 2002).
Heenan, M., et al., "Methotrexate induces apoptotic cell death in human keratinocytes," *Arch. Dermatol. Res.* 290:240-245, Springer-Verlag (1998).
Infante, A.J., et al., "The clinical spectrum in a large kindred with autoimmune lymphoproliferative syndrome caused by a Fas mutation that impairs lymphocyte apoptosis," *J. Pediatr.* 133:629-633, Mosby, Inc. (1998).
Kalemkerian, G.P., and Ou, X., "Activity of fenretinide plus chemotherapeutic agents in small-cell lung cancer cell lines," *Cancer Chemother. Pharmacol.* 43:145-150, Springer-Verlag (1999).
Kelland, L.R., et al., "Preclinical Antitumor Activity and Pharmacodynamic Studies with the Farnesyl Protein Transferase Inhibitor R115777 in Human Breast Cancer," *Clin. Cancer Res.* 7:3544-3550, American Association for Cancer Research (Nov. 2001).
Kyprianou, N., and Benning, C.M., "Supression of Human Prostate Cancer Cell Growth By α1-Adrenoceptor Antagonists Doxazosin and Terazosin via Induction of Apoptosis," *Cancer Res.* 60:4550-4555, American Association for Cancer Research (2000).
Leong, Y-W. et al., "Forbesione, a Modified Xanthone from *Garcinia forbesii*," *J. Chem. Res. Synop.*, Issue 8:392-393, The Royal Society of Chemistry (1996).
Lin, L-J., et al., "Isogambogic acid and Isomorellinol from *Garcinia hanburyi*," *Magn. Reson. Chem.* 31:340-347, John Wiley & Sons, Ltd. (1993).
Liu, W.M., et al., "The *in vitro* activity of the tyrosine kinase inhibitor ST1571 in BCR-ABL positive chronic myeloid leukaemia cells: synergistic interactions with anti-leukaemic agents," *Br. J. Cancer* 86:1472-1478, Nature Publishing Group on behalf of Cancer Research UK (May 2002).
López-Hoyos, M., et al., "Regulation of B cell apoptosis by Bcl-2 and Bcl-$X_L$ and its role in the development of autoimmune diseases (Review)," *Int. J. Mol. Med.* 1:475-483, D.A. Spandidos (1998).
Los, M., et al., "Cross-Resistance of CD95- and Drug-Induced Apoptosis as a Consequence of Deficient Activation of Caspases (ICE/Ced-3 Proteases)," *Blood* 90:3118-3129, American Society of Hematology (1997).
Lu, G-B., et al., "Isolation and Structure of neo-Gambogic Acid from Gamboge (*Garcinia hanburryi*)," *Yaoxue Xuebao [Acta Pharmaceutica Sinica]* 19:636-639, Beijing: Zhongguo yao xue hui (1984).
Lu, G., et al., "Isolation and structure of neo-gambogic acid from gamboge (*Garcinia hanburryi*)," *Chemical Abstracts* 102:395, Abstract No. 102:21181z, American Chemical Society (1985).
Motwani, M., et al., "Augmentation of Apoptosis and Tumor Regression by Flavopiridol in the Presence of CPT-11 in Hct116 Colon Cancer Monolayers and Xenografts," *Clin. Cancer Res.* 7:4209-4219, American Association for Cancer Research (Dec. 2001).
Ohsako, S., and Elkon, K.B., "Apoptosis in the effector phase of autoimmune diabetes, multiple sclerosis and thyroiditis," *Cell Death Differ.* 6:13-21, Stockton Press (1999).
Ollis, W.D., et al., "The Constitution of Gambogic Acid," *Tetrahedron* 21:1453-1470, Pergamon Press, Ltd. (1965).
O'Reilly, L.A., and Strasser, A., "Apoptosis and autoimmune disease," *Inflamm. res.* 48:5-21, Birkhäuser Verlag (1999).
Ozawa, M., et al., "312-nanometer Ultraviolet B Light (Narrow-Band UVB) Induces Apoptosis of T Cells within Psoriatic Lesions," *J. Exp. med.* 189:711-718, Rockefeller University Press (1999).
Rukachaisirikul, V., et al., "Caged-Tetraprenylated Xanthones from *Garcinia scortechinii*," *Tetrahedron* 56:8539-8543, Elsevier Science, Ltd. (2000).
Savill, J., "Apoptosis in resolution of inflammation," *J. Leukocyte Biol.* 61:375-380, Society for Leukocyte Biology (1997).
Schmitt, E., et al., "Bcl-xL and Bax-α control points: modulation of apoptosis induced by cancer chemotherapy and relation to TPCK-sensitive protease and caspase activation," *Biochem. Cell Biol.* 75:301-314, National Research Council of Canada (1997).
Subba Rao, G.S.R., et al., "Structure of moreollin, a pigment isolated from *Garcinia morella* Desser," *Proc. Indian Acad. Sci.* 87 A (*Chem. Sci.*):75-86, Indian National Science Academy (1978).
Tai, D.I., et al., "Activation of Nuclear Factor κB in Hepatits C Virus Infection: Implications for Pathogenesis and Hepatocarcinogenesis," *Hepatology* 31:656-664, W.B. Saunders Company (Mar. 2000).
Thoison, O., et al., "Cytotoxic Prenylxanthones from *Garcinia bracteata*," *J. Nat. Prod.* 63:441-446, American Chemical Society and American Society of Pharmacognosy (Published on Web Mar. 10, 2000).
Vaishnaw, A.K., et al., "The molecular basis for apoptotic defects in patients with CD95 (Fas/Apo-2) mutations," *J. Clin. Invest.* 103:355-363, American Society for Clinical Investigation (1999).
Vilner, B.J., et al., "Sigma-1 and Sigma-2 Receptors Are Expressed in a Wide Variety of Human and Rodent Tumor Cell Lines," *Cancer Res.* 55: 408-413, American Association for Cancer Research (1995).
Wakisaka, S., et al., "Modulation by proinflammatory cytokines of Fas/Fas ligand-mediated apoptotic cell death of synovial cells in patients with rheumatoid arthritis (RA)," *Clin. Exp. Immunol.* 114:119-128, Blackwell Science (1998).
Wu, J., et al., "A highly rearranged tetraprenylxanthonoid from *Garcinia gaudichaudii* (Guttiferae)," *Tetrahedron lett.* 42:727-729, Elsvier Science, Ltd. (Jan. 2001).
Wu, X. et al., "Mitochondrial Destabilisation and Caspase-3 Activation are Involved in the Apoptosis of Jurkat Cells Induced by Gaudichaudione A, a Cytotoxic Xanthone," *Planta Med.* 68:198-203, Georg Thieme Verlag (Mar. 2003).
Xu, Y.J., et al., "Novel Cytotoxic, Polyprenylated Heptacycllic Xanthonoids from Indonesian *Garcinia gaudichaudii* (Guttiferae)," *Organic Lett.* 2:3945-3948, American Chemical Society (2000).
Zhou, T., et al., "Bisindolylmaleimide VIII facilitates Fas-mediated apoptosis and inhibits T cell-mediated autoimmune diseases," *Nat. med.* 5:42-48, Nature Publishing Company (1999).
Zou, C., et al., "Combined effect of chemopreventative agent N-(4-hydroxyphenyl) retinamide (4-HPR) and γ-radiation on bladder cancer cell lines," *Int. J. Oncol.* 13:1037-1041, D.A. Spandidos (1998).
Karanjgaonkar, C.G., et al., "Morellic, Isomorellic and Gambogic Acids," *Tetrahedron Lett. No. 7*: 687-691, Pergamon Press, Ltd. (1966).

Martinou, J-C., and Antonsson, B., "Bax, a Proapoptotic Protein Forming Channels in mitochondria," in *Apoptosis and Cancer Chemotherapy*, Hickman, J.A., and Dive, C., ed., Humana Press, Inc., Totowa, NJ, pp. 129-141 (1999).

Yates, P., et al., "Acetyl-α-Gambogic Acid," *Tetrahedron Lett. No. 24*:1623-1629, Pergamon Press, Ltd. (1963).

Bradley, M.O., et al., "Tumor Targeting by Covalent Conjugation of a Natural Fatty Acid to Paclitaxel," *Clin. Cancer Res. 7*:3229-3238, The American Association for Cancer Research (Oct. 2001).

Nagy, A., et al., "Cytotoxic analogs of luteinizing hormone-releasing hormone containing doxorubicin or 2-pyrrolinodoxorubicin, a derivative 500-1000 times more potent," *Proc. Natl. Acad. Sci. USA 93*:7269-7273, National Academy of Sciences (1996).

Sievers, E.L., and Linenberger, M., "Mylotarg: antibody-targeted chemotherapy comes of age," *Curr. Opin. Oncol. 13*:522-527, Lippincott Williams & Wilkins, Inc. (Nov. 2001).

DERIVATIVES OF GAMBOGIC ACID AND ANALOGS AS ACTIVATORS OF CASPASES AND INDUCERS OF APOPTOSIS

STATEMENT REGARDING FEDERALLY-SPONSORED RESEARCH AND DEVELOPMENT

This invention was made in part with government support under DHHS Grant No. 1R43 CA91811-01 awarded by the National Cancer Institute. The U.S. Government has certain rights to the invention.

BACKGROUND OF THE INVENTION

1. Field of the Invention

This invention is in the field of medicinal chemistry. In particular, the invention relates to derivatives of gambogic acid and analogs, and the discovery that these compounds are activators of caspases and inducers of apoptosis. The invention also relates to the use of these compounds as therapeutically effective anti-cancer agents.

2. Description of Background Art

Organisms eliminate unwanted cells by a process variously known as regulated cell death, programmed cell death or apoptosis. Such cell death occurs as a normal aspect of animal development, as well as in tissue homeostasis and aging (Glucksmann, A., *Biol. Rev. Cambridge Philos. Soc.* 26:59–86 (1951); Glucksmann, A., *Archives de Biologie* 76:419–437 (1965); Ellis, et al., *Dev.* 112:591–603 (1991); Vaux, et al., *Cell* 76:777–779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane-enclosed particles containing intracellular material) (Orrenius, S., *J. Internal Medicine* 237:529–536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9–34). A cell activates its internally-encoded suicide program as a result of either internal or external signals. The suicide program is executed through the activation of a carefully regulated genetic program (Wyllie, et al., *Int. Rev. Cyt.* 68:251 (1980); Ellis, et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529–536 (1995)).

It has been found that a group of proteases are a key element in apoptosis (see, e.g. Thornberry, *Chemistry and Biology* 5:R97-R103 (1998); Thornberry, *British Med. Bull.* 53:478–490 (1996)). Genetic studies in the nematode *Caenorhabditis elegans* revealed that apoptotic cell death involves at least 14 genes, 2 of which are the pro-apoptotic (death-promoting) ced (for cell death abnormal) genes, ced-3 and ced-4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (*Apoptosis and Cancer Chemotherapy*, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become immortal—they become cancerous. In the case of the apoptosis process, control points are known to exist that represent points for intervention leading to activation. These control points include the CED-9—BCL-like and CED-3—ICE-like gene family products, which are intrinsic proteins regulating the decision of a cell to survive or die and executing part of the cell death process itself, respectively (Schmitt, et al., *Biochem. Cell. Biol.* 75:301–314 (1997)). BCL-like proteins include BCL-xL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los et al., *Blood*, 90(8):3118–3129 (1997); Friesen, et al., *Nat. Med.* 2:574 (1996)). The mechanism of action of current antineoplastic drugs frequently involves an attack at specific phases of the cell cycle. In brief, the cell cycle refers to the stages through which cells normally progress during their lifetime. Normally, cells exist in a resting phase termed $G_o$. During multiplication, cells progress to a stage in which DNA synthesis occurs, termed S. Later, cell division, or mitosis, occurs in a phase called M. Antineoplastic drugs such as cytosine arabinoside, hydroxyurea, 6-mercaptopurine, and methotrexate are S phase specific, whereas antineoplastic drugs such as vincristine, vinblastine, and paclitaxel are M phase specific. Many slow growing tumors, e.g. colon cancers, exist primarily in the $G_o$ phase, whereas rapidly proliferating normal tissues, e.g. bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (see, e.g., Hardman, et al., eds., *Goodman and Gilman's The Pharmacological Basis of Therapeutics*, Ninth Edition, McGraw-Hill, New York (1996), pp. 1225–1287). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducers of apoptosis is a highly desirable goal in the development of therapeutically-effective antineoplastic agents. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

Gambogic acid was isolated from gamboge and the structure was deduced from the $^1$H NMR spectrum and by comparison with morellin, which also has the xanthone structure as that of gambogic acid (Ahmad, S. A., et al. *J. Chem. Soc.* (C) 772–779 (1966); Ollis, W. D., et al. *Tetrahedron*, 21:1453–1470 (1965)).

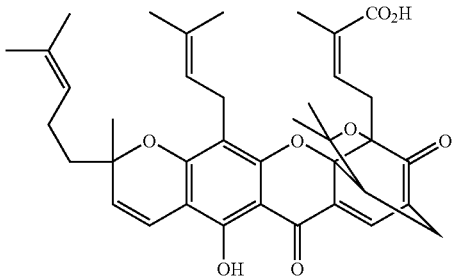

Asano J., et al., *Phytochemistry*, 41:815–820 (1996), reported the isolation of several xanthones, including gambogic acid from gamboge. They reported that gambogic acid is cytotoxic to both HeLa and HEL cells.

Lin, L.-J., et al., *Magn. Reson. Chem.* 31:340–347 (1993), reported the isolation of gambogic acid, as well as isogambogic acid and isomorellinol. All 3 compounds were reported to be cytotoxic against KB and KB-V1 cell lines.

WO00/44216 disclosed gambogic acid, analogs and derivatives as activators of caspases and inducers of apoptosis.

SUMMARY OF THE INVENTION

The present invention is related to the discovery that derivatives of gambogic acid and analogs, as represented in Formulae I and II, are activators of the caspase cascade and inducers of apoptosis. Therefore, the first aspect of the present invention is directed to the use of compounds of Formulae I and II as inducers of apoptosis.

A second aspect of the present invention is directed to a method of treating, preventing or ameliorating a disorder responsive to the induction of apoptosis in an animal suffering therefrom, comprising administering to a mammal in need of such treatment an effective amount of a compound having one of the Formulae I–II:

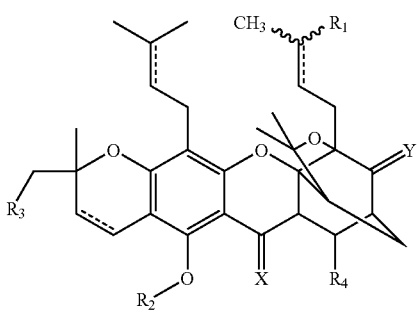

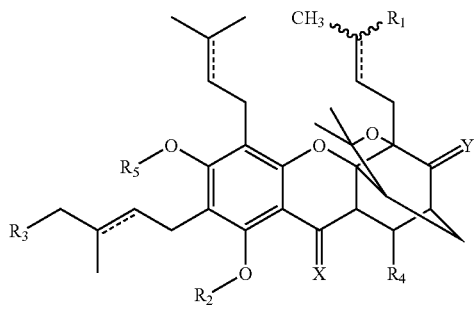

or pharmaceutically acceptable salts or prodrugs thereof, wherein:

the dotted lines are single bonds, double bonds or an epoxy group;

X together with the attached carbon is a methylene, carbonyl, hydroxymethinyl, alkoxymethinyl, aminomethinyl, an oxime, a hydrazone, an arylhydrazone or semicarbazone;

Y together with the attached carbon is a methylene, carbonyl, hydroxymethinyl, alkoxymethinyl, aminomethinyl, an oxime, a hydrazone, an arylhydrazone or semicarbazone;

$R_1$ is formyl, methylenehydroxy, carboxy, acyl ($R_aCO$), optionally substituted alkoxycarbonyl ($R_aOCO$), optionally substituted alkylthiocarbonyl, optionally substituted aminocarbonyl (carbamyl, $R_bR_cNCO$) or hydroxyaminocarbonyl, where $R_a$ is hydrogen, optionally substituted lower alkyl, optionally substituted aryl, or optionally substituted lower aralkyl group; $R_b$ and $R_c$ are independently hydrogen, optionally substituted lower alkyl, optionally substituted aryl, or optionally substituted lower aralkyl groups; or $R_a$ is the group $—(CH_2CH_2O)_nR_m$ wherein n=1–10 and $R_m$ is hydrogen or $C_{1-10}$ alkyl; or $R_b$ and $R_c$ may be taken together with the attached N to form a heterocycle, including piperidine, morpholine and piperazine;

$R_2$ is hydrogen, optionally substituted alkyl, acyl ($R_aCO$), carbamyl ($R_bR_cNCO$) or sulfonyl ($R_dSO_2$), where $R_a$, $R_b$ and $R_c$ are defined above; $R_d$ is hydrogen, optionally substituted lower alkyl, optionally substituted aryl, or optionally substituted lower aralkyl groups;

$R_3$ is hydrogen or prenyl;

$R_4$ is hydrogen, halogen, hydroxy, optionally substituted alkyl, cycloalkyl, alkoxy, arylalkoxy, aryloxy, heteroaryloxy, alkylthio, arylalkylthio, arylthio, heteroarylthio, amino, aminoalkoxy, optionally substituted saturated or partially saturated heterocyclo, heterocycloalkoxy or heterocycloalkylamino; and $R_5$ is hydrogen, optionally substituted alkyl or acyl ($R_aCO$), carbamyl ($R_bR_cNCO$) or sulfonyl ($R_dSO_2$), where $R_a$, $R_b$, $R_c$ and $R_d$ are defined above; wherein said compound causes no tissue damage or cell death as a result of side effects arising from administering said compound.

A third aspect of the present invention is to provide a method for treating, preventing or ameliorating neoplasia and cancer by administering a compound of Formulae I and II to a mammal in need of such treatment.

A fourth aspect of the present invention is to provide novel compounds of Formulae I and II, and to also provide for the use of these novel compounds for treating, preventing or ameliorating neoplasia and cancer.

A fifth aspect of the present invention is to provide a pharmaceutical composition useful for treating disorders responsive to the induction of apoptosis, containing an effective amount of a compound of Formulae I and II in admixture with one or more pharmaceutically acceptable carriers or diluents.

A sixth aspect of the present invention is directed to methods for the preparation of novel compounds of Formulae I and II.

DETAILED DESCRIPTION OF THE INVENTION

The present invention arises out of the discovery that derivatives of gambogic acid are potent and highly efficacious activators of the caspase cascade and inducers of apoptosis. Therefore, these compounds are useful for treating disorders responsive to induction of apoptosis.

There are many functional groups in the structure of gambogic acid which can be modified. These include, but are not limited to, the carboxyl group, which can be converted to an ester, amide, ketone or alcohol and other functional groups. The ester and amide can also contain other functional groups, such as a carboxyl in an amino acid, for further modification; the hydroxy group, which can be converted to an ether or ester and other functional groups; the carbon-carbon double bond in the α,β-unsaturated ketone, which can react with a nucleophile, or be reduced to a carbon-carbon single bond, or be converted to an epoxide, and undergo other reactions; the carbon-carbon double bond in the α,β-unsaturated carboxyl, which also can react with a nucleophile, or be reduced to a carbon-carbon single bond, or be converted to a cyclopropane ring, and undergo other reactions; the two isoprene carbon-carbon double bonds, which can be reduced to a carbon-carbon single bond, or be converted to an epoxide, which can then undergo other reactions, or be cleaved to form an aldehyde or carboxyl group, which also can be modified to other functional groups; the carbon-carbon double bond in the left ring also can be reduced to a carbon-carbon single bond, or be converted to an epoxide, and undergo other reactions; the ketone group in the right ring can be reduced to an alcohol, or be converted to an oxime or a semicarbazone, or be converted to an amino group; the other ketone group also can be reduced, or be converted to other functional groups. Therefore, many derivatives of gambogic acid can be prepared.

In addition, analogs of gambogic acid, including isomorellin, morellic acid, desoxymorellin, gambogin, morelline dimethyl acetal, isomoreollin B, Moreollic acid, gambogenic acid, gambogenin, isogambogenin, desoxygambogenin, gambogenin dimethyl acetal, gambogellic acid, hanburin (Asano, J., et al., *Phytochemistry* 41:815–820 (1996)), isogambogic acid, isomorellinol (Lin, L.-J., et al, *Magn. Reson. Chem.* 31:340–347 (1993)) and neo-gambogic acid (Lu, G. B., et al., *Yao Hsueh Hsueh Pao* 19:636–639 (1984)) can be isolated from gamboge. Other analogs of gambogic acid, including morellin, desoxymorellin, dihydroisomorellin (Bhat et al. *Indian J. Chem.* 2:405–409 (1964)) and moreollin (Rao et al. *Proc. Indian Acad. Sci.* 87A:75–86 (1978)) can be isolated from the seed of *Garcinia morella*. Morellinol can be isolated from the bark of *Garcinia morella* (Adawadkar et al. *Indian J. Chem.* 14B:19–21 (1976)). Gaudichaudiones (A-H) and gaudichaudiic acids (A-E) can be isolated from the leaves of *garcinia Gaudichaudii* (Guttiferae) (Cao, S. G., et al., *Tetrahedron* 54(36):10915–10924 (1998), Cao, S. G., et al., *Tetrahedron Lett.* 39(20):3353–3356 (1998), and Wu, X. et al., *Planta Med.* 68:198–203, (2002)). Forbesione can be isolated from *Garcinia forbesii* (Leong, Y. W., et al., *J. Chem. Res., Synop.* 392–393 (1996)). Bractatin, isobractatin, 1-0-methylbractatin, 1-0-methylisobractatin, 1-0-methyl-8-methoxy-8,8a-dihydrobractatin, and 1-0-methylneobractatin can be isolated from a leaf extract of *G. bracteata* (Thoison, O., et al., *J. Nat. Prod.* 63:441–446 (2000)). Novel gaudichaudiic acids (F-I) can be isolated from the bark of Indonesian *Garcinia gaudichaudii* (Xu, Y., et al., *Organic Lett.* 2(24):3945–3948 (2000)). Scortechinones (A-C) can be isolated from twigs of *Garcinia scortechinii* (Rukachaisirikul, V., et al., *Tetrahedron* 56:8539–8543 (2000)). Gaudispirolactone can be isolated from the bark of *Garcinia gaudichaudii* (Wu, J., et al., *Tetrahedron Lett.* 42:727–729 (2001)). These gambogic acid analogs also can be used for the preparation of derivatives similar to gambogic acid.

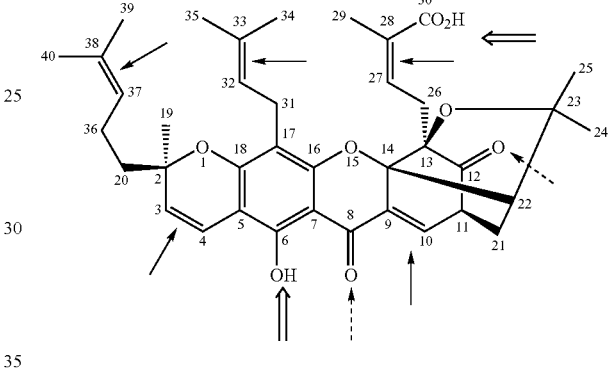

The present invention, therefore, also arises out of the discovery that novel derivatives of gambogic acid analogs are activators of the caspase cascade and inducers of apoptosis. Therefore, these derivatives and analogs of gambogic acid are useful for treating disorders responsive to the induction of apoptosis.

The present invention also arises out of the discovery that the double bond in the 9–10 positions of gambogic acid is critical for activity, and the Michael addition to this double bond by certain nucleophiles are reversible. This reversibility can be explored to reduce the toxicity of gambogic acid and its analogs and derivatives.

Specifically, compounds useful in this aspect of the present invention are derivatives of gambogic acid and its analogs as represented by Formulae I and II:

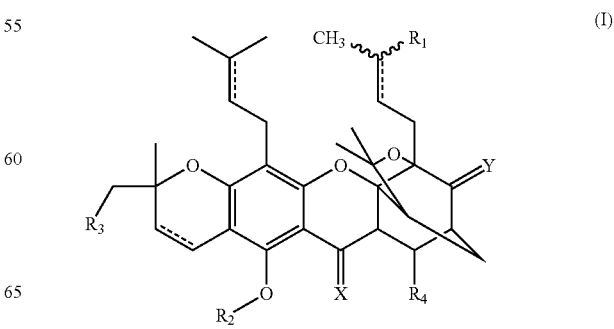

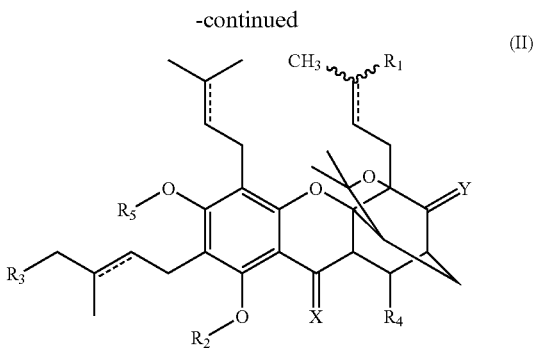
(II)

or pharmaceutically acceptable salts or prodrugs thereof, wherein: the dotted lines are single bonds, double bonds or an epoxy group;

X together with the attached carbon is a methylene, carbonyl, hydroxymethinyl, alkoxymethinyl, aminomethinyl, an oxime, a hydrazone, an arylhydrazone or semicarbazone;

Y together with the attached carbon is a methylene, carbonyl, hydroxymethinyl, alkoxymethinyl, aminomethinyl, an oxime, a hydrazone, an arylhydrazone or semicarbazone;

$R_1$ is formyl, methylenehydroxy, carboxy, acyl ($R_aCO$), optionally substituted alkoxycarbonyl ($R_aOCO$), optionally substituted alkylthiocarbonyl, optionally substituted aminocarbonyl (carbamyl, $R_bR_cNCO$) or hydroxyaminocarbonyl, where $R_a$ is hydrogen, optionally substituted lower alkyl, optionally substituted lower alkoxy, optionally substituted aryl, or optionally substituted lower aralkyl group; $R_b$ and $R_c$ are independently hydrogen, optionally substituted lower alkyl, optionally substituted aryl, or optionally substituted lower aralkyl groups; or $R_a$ is the group $-(CH_2CH_2O)_nR_m$ wherein n=1–10 and $R_m$ is hydrogen or $C_{1-10}$ alkyl; or $R_b$ and $R_c$ may be taken together with the attached N to form a heterocycle, including piperidine, morpholine and piperazine;

$R_2$ is hydrogen, optionally substituted alkyl, acyl ($R_aCO$), carbamyl ($R_bR_cNCO$) or sulfonyl ($R_dSO_2$), where $R_a$, $R_b$ and $R_c$ are defined above; $R_d$ is hydrogen, optionally substituted lower alkyl, optionally substituted aryl, or optionally substituted lower aralkyl groups;

$R_3$ is hydrogen or prenyl;

$R_4$ is hydrogen, halogen, hydroxy, optionally substituted alkyl, cycloalkyl, alkoxy, arylalkoxy, aryloxy, heteroaryloxy, alkylthio, arylalkylthio, arylthio, heteroarylthio, amino, aminoalkoxy, optionally substituted saturated or partially saturated heterocyclo, heterocycloalkoxy or heterocycloalkylamino; and $R_5$ is hydrogen, optionally substituted alkyl or acyl ($R_aCO$), carbamyl ($R_bR_cNCO$) or sulfonyl ($R_dSO_2$), where $R_a$, $R_b$, $R_c$ and $R_d$ are defined above.

Preferred compounds falling within the scope of Formulae I and II include compounds wherein $R_1$ is formyl, acetyl, propionyl, carboxy, methoxy carbonyl, ethoxycarbonyl, propoxycarbonyl, butoxycarbonyl, isobutoxycarbonyl, 2-hydroxyethoxycarbonyl, 2-{2-[2-(2-methoxyethoxy)-ethoxy]ethoxy}ethoxycarbonyl, 2-[2-(2-ethoxyethoxy)ethoxy]ethoxycarbonyl, 2-{2-[2-(2-octyloxyethoxy)ethoxy]ethoxy}ethoxycarbonyl, methylthiocarbonyl, ethylthiocarbonyl, butylthiocarbonyl, dimethylcarbamyl, diethylcarbamyl, N-piperidinylcarbonyl, N-methyl-N-piperazinylcarbonyl, 2-(dimethylamino)ethylcarboxy or N-morpholinylcarbonyl; $R_2$ is hydrogen, formyl, acetyl, dimethylcarbamyl, diethylcarbamyl, 2-(dimethylamino) ethylcarbamyl, 1-piperidinylcarbonyl, N-methyl-N-piperazinylcarbonyl, N-morpholinylcarbonyl, methylsulfonyl, ethylsulfonyl, phenylsulfonyl, methyl, ethyl, 2-piperidinylethyl, 2-morpholinylethyl, 2-(dimethylamino)ethyl, or 2-(diethylamino)ethyl; $R_4$ is chloro, bromo, hydroxy, hydrogen, methoxy, ethoxy, phenoxy, benzyloxy, methylthio, ethylthio, butylthio, phenylthio, dimethylamino, diethylamino, piperidinyl, piperazinyl, pyrrolidinyl, imidazolyl, pyrazolyl, N-methylpiperazinyl, 2-(dimethylamino) ethylamino, morpholinyl, anilino, 4-acetylpiperazinyl, 2-(morpholinyl)-ethylamino, 4-(2-pyridyl)piperazinyl, 2-(morpholinyl)ethoxy, or 2-dimethyl-aminoethoxy; X and Y is O; $R_3$ is prenyl; and the dotted lines are double bonds. If the double bond is present at C27–28, it is preferred that it has the Z configuration.

Exemplary preferred compounds that may be employed in the method of invention include, without limitation:

9,10-Dihydro-10-morpholinyl-gambogyl (N-methylpiperazine);

9,10-Dihydro-10-piperidinyl-gambogyl (N-methylpiperazine);

9,10-Dihydro-10-[2-(morpholinyl)ethylamino]-gambogyl (N-methylpiperazine);

9,10-Dihydro-10-[4-(2-pyridyl)piperazinyl]-gambogyl (N-methylpiperazine);

9,10-Dihydro-10-[2-(morpholinyl)ethoxy]-gambogyl (N-methylpiperazine);

9,10-Dihydro-10-(2-dimethylaminoethoxy)-gambogyl (N-methylpiperazine);

9,10-Dihydro-10-morpholinyl-gambogyl morpholine;

9,10-Dihydro-10-ethoxy-gambogyl piperidine;

9,10-Dihydro-10-morpholinyl-gambogyl (dimethylamine);

Ethyl 9,10-dihydro-10-morpholinyl-gambogate;

Methyl 9,10-dihydro-10-benzyloxy-gambogate;

Methyl 9,10-dihydro-10-(4-acetylpiperazinyl)-gambogate;

Methyl 9,10-dihydro-10-(piperidinyl)-gambogate;

9,10-Dihydro-10-[4-(2-pyridyl)piperazinyl]-gambogyl (diethylamine);

9,10-Dihydro-10-[4-(2-pyridyl)piperazinyl]-gambogyl (methylamine);

9,10-Dihydro-10-(morpholinyl)-gambogyl (diethylamine);

Methyl-9,10-dihydro-10-ethoxy-gambogate;

9,10-Dihydro-10-ethoxy-gambogic acid;

9,10-Dihydro-10-ethoxy-gambogyl (diethylamine);

Ethyl 9,10-dihydro-10-ethoxy-gambogate;

Methyl 9,10-dihydro-10-(4-methylpiperazinyl)-gambogate;

Ethyl 9,10-dihydro-10-(piperidinyl)-gambogate;

Ethyl 9,10-dihydro-10-(4-methylpiperazinyl)-gambogate; and

Ethyl 9,10-dihydro-10-(4-acetylpiperazinyl)-gambogate.

The positions in gambogic acid are numbered according to Asano, J., et al., *Phytochemistry* 41:815–820 (1996), and Lin, L.-J., et al., *Magn. Reson. Chem.* 31:340–347 (1993).

Other preferred compounds that may be employed in this invention include, without limitation:

9,10-Dihydro-10-morpholinyl-gambogyl morpholine;

9,10-Dihydro-10-morpholinyl-gambogyl piperidine;

9,10-Dihydro-10-(4-methylpiperazinyl)-gambogyl piperidine;

9,10-Dihydro-10-(4-methylpiperazinyl)-gambogyl morpholine;
9,10-Dihydro-10-piperidinyl-gambogyl piperidine;
9,10-Dihydro-10-(4-methylpiperazinyl)-gambogyl methylpiperazine);
9,10-Dihydro-10-methoxy-gambogic acid;
9,10-Dihydro-10-butylthio-gambogic acid;
9,10-Dihydro-10-(4-methylpiperazinyl)-gambogic acid;
9,10-Dihydro-10-pyrrolidinyl-gambogic acid;
Methyl 9,10-Dihydro-10-morpholinyl-gambogate;
9,10-Dihydro-10-piperidinyl-gambogic acid;
9,10-Dihydro-10-morpholinyl-gambogic acid;
9,10-Dihydro-10-(4-(2-pyridyl)piperazinyl)gambogyl (4-(2-pyridyl)piperazine);
9,10-Dihydro-10-(4-(2-pyridyl)piperazinyl)gambogic acid; and
9,10-Dihydro-10-methoxy-gambogyl piperidine.

Other preferred compounds that may be employed in this invention include, without limitation:
2-{2-[2-(2-Octyloxyethoxy)ethoxy]ethoxy}ethyl Gambogate;
2-{2-[2-(2-Octyloxyethoxy)ethoxy]ethoxy}ethyl 9,10-Dihydro-10-morpholinyl gambogate;
2-[2-(2-Ethoxyethoxy)ethoxy]ethyl Gambogate;
2-[2-(2-Ethoxyethoxy)ethoxy]ethyl 9,10-Dihydro-10-morpholinyl gambogate;
Propyl Gambogate;
Propyl 9,10-Dihydro-10-morpholinyl-gambogate;
2-{2-[2-(2-Methoxyethoxy)ethoxy]ethoxy}ethyl gambogate;
2-{2-[2-(2-Methoxyethoxy)ethoxy]ethoxy}ethyl 9,10-Dihydro-10-morpholinyl-gambogate;
2-Hydroxyethyl Gambogate;
2-Hydroxyethyl 9,10-Dihydro-10-morpholinyl-gambogate;
Methyl 9,10-Dihydro-gambogate;
Methyl 9,10,12-Trihydro-12-hydroxy-gambogate;
Methyl 32,33-Epoxy-37,38-epoxy-gambogate;
Methyl 37,38-Epoxy gambogate;
Methyl 9,10-Epoxy-gambogate;
Butyl Gambogate;
Isobutyl Gambogate;
Butyl 9,10-Dihydro-10-morpholinyl-gambogate;
Isobutyl 9,10-Dihydro-10-morpholinyl-gambogate;
3,4,9,10,32,33,37,38-Octahydro-gambogic Acid;
Ethyl 3,4,9,10,32,33,37,38-Octahydro-10-morpholinyl-gambogate;
Ethyl 3,4,32,33,37,38-Hexahydro-gambogate;
Ethyl 12-Hydro-12-hydroxy-gambogate;
Ethyl 9,10,12-Trihydro-12-hydroxy-gambogate;
Ethyl 3,4,9,10,27,28,32,33,37,38-Decahydro-10-morpholinyl-gambogate; and
Ethyl 3,4,27,28,32,33,37,38-Octahydro-gambogate.

The present invention is also directed to novel compounds within the scope of Formulae I and II. Exemplary preferred compounds that may be employed in this invention include, without limitation:
9,10-Dihydro-10-morpholinyl-gambogyl (N-methylpiperazine);
9,10-Dihydro-10-piperidinyl-gambogyl (N-methylpiperazine);
9,10-Dihydro-10-[2-(morpholinyl)ethylamino]-gambogyl (N-methylpiperazine);
9,10-Dihydro-10-[4-(2-pyridyl)piperazinyl]-gambogyl (N-methylpiperazine);
9,10-Dihydro-10-[2-(morpholinyl)ethoxy]-gambogyl (N-methylpiperazine);
9,10-Dihydro-10-(2-dimethylaminoethoxy)-gambogyl (N-methylpiperazine);
9,10-Dihydro-10-morpholinyl-gambogyl morpholine;
9,10-Dihydro-10-ethoxy-gambogyl piperidine;
9,10-Dihydro-10-morpholinyl-gambogyl (dimethylamine);
Ethyl 9,10-dihydro-10-morpholinyl-gambogate;
Methyl 9,10-dihydro-10-benzyloxy-gambogate;
Methyl 9,10-dihydro-10-(4-acetylpiperazinyl)-gambogate;
Methyl 9,10-dihydro-10-(piperidinyl)-gambogate;
9,10-Dihydro-10-[4-(2-pyridyl)piperazinyl]-gambogyl (diethylamine);
9,10-Dihydro-10-[4-(2-pyridyl)piperazinyl]-gambogyl (methylamine);
9,10-Dihydro-10-(morpholinyl)-gambogyl (diethylamine);
Methyl-9,10-dihydro-10-ethoxy-gambogate;
9,10-Dihydro-10-ethoxy-gambogic acid;
9,10-Dihydro-10-ethoxy-gambogyl (diethylamine);
Ethyl 9,10-dihydro-10-ethoxy-gambogate;
Methyl 9,10-dihydro-10-(4-methylpiperazinyl)-gambogate;
Ethyl 9,10-dihydro-10-(piperidinyl)-gambogate;
Ethyl 9,10-dihydro-10-(4-methylpiperazinyl)-gambogate; and
Ethyl 9,10-dihydro-10-(4-acetylpiperazinyl)-gambogate.

Other novel preferred compounds that may be employed in this invention include, without limitation:
2-{2-[2-(2-Octyloxyethoxy)ethoxy]ethoxy}ethyl 9,10-Dihydro-10-morpholinyl gambogate;
2-[2-(2-Ethoxyethoxy)ethoxy]ethyl 9,10-Dihydro-10-morpholinyl gambogate;
Propyl 9,10-Dihydro-10-morpholinyl-gambogate;
2-{2-[2-(2-Methoxyethoxy)ethoxy]ethoxy}ethyl 9,10-Dihydro-10-morpholinyl-gambogate;
2-Hydroxyethyl 9,10-Dihydro-10-morpholinyl-gambogate;
Methyl 9,10-Epoxy-gambogate;
Butyl 9,10-Dihydro-10-morpholinyl-gambogate;
Isobutyl 9,10-Dihydro-10-morpholinyl-gambogate;
Ethyl 3,4,9,10,32,33,37,38-Octahydro-10-morpholinyl-gambogate;
Ethyl 3,4,9,10,27,28,32,33,37,38-Decahydro-10-morpholinyl-gambogate; and
9,10-Dihydro-10-(morpholinyl)-gambogyl methylamine.

Other novel preferred compounds that may be employed in this invention include, without limitation:
Ethyl gambogate; and
Gambogyl methylamine.

Other novel preferred compounds that may be employed in this invention include, without limitation:
2-{2-[2-(2-Octyloxyethoxy)ethoxy]ethoxy}ethyl Gambogate;
2-[2-(2-Ethoxyethoxy)ethoxy]ethyl Gambogate;
Propyl Gambogate;
2-{2-[2-(2-Methoxyethoxy)ethoxy]ethoxy}ethyl gambogate;
2-Hydroxyethyl Gambogate;
Methyl 9,10-Dihydro-gambogate;
Methyl 9,10,12-Trihydro-12-hydroxy-gambogate;
Methyl 32,33-Epoxy-37,38-epoxy-gambogate;
Methyl 37,38-Epoxy gambogate;
Butyl Gambogate;
Isobutyl Gambogate;
3,4,9,10,32,33,37,38-Octahydro-gambogic Acid;
Ethyl 3,4,32,33,37,38-Hexahydro-gambogate;

Ethyl 12-Hydro-12-hydroxy-gambogate;

Ethyl 9,10,12-Trihydro-12-hydroxy-gambogate; and

Ethyl 3,4,27,28,32,33,37,38-Octahydro-gambogate.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups, which can be optionally substituted.

Useful alkoxy groups include oxygen substituted by one of the $C_{1-10}$ alkyl groups mentioned above, which can be optionally substituted.

Useful alkylthio groups include sulphur substituted by one of the $C_{1-10}$ alkyl groups mentioned above, which can be optionally substituted. Also included are the sulfoxides and sulfones of such alkylthio groups.

Useful amino groups include $-NH_2$, $-NHR_{11}$, and $-NR_{11}R_{12}$, wherein $R_{11}$ and $R_{12}$ are $C_{1-10}$ alkyl or cycloalkyl groups, aryl or heteroaryl groups, or arylalkyl or heteroarylalkyl groups, or $R_{11}$ and $R_{12}$ are combined with the N to form a cycloamino structure, such as a piperidine, or $R_{11}$ and $R_{12}$ are combined with the N and other groups to form a cycloamino structure, such as a piperazine. The alkyl, cycloalkyl, aryl, heteroaryl, cycloamino groups can be optionally substituted.

Optional substituents on the alkyl groups include one or more halo, hydroxy, carboxyl, amino, nitro, cyano, $C_1$–$C_6$ acylamino, $C_1$–$C_6$ acyloxy, $C_1$–$C_6$ alkoxy, aryloxy, alkylthio, $C_6$–$C_{10}$ aryl, $C_4$–$C_7$ cycloalkyl, $C_2$–$C_6$ alkenyl, $C_2$–$C_6$ alkynyl, $C_6$–$C_{10}$ aryl($C_2$–$C_6$)alkenyl, $C_6$–$C_{10}$ aryl($C_2$–$C_6$) alkynyl, saturated and unsaturated heterocyclic, or heteroaryl. Optional substituents on the aryl, aralkyl and heteroaryl groups include one or more halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$)alkyl, $C_6$–$C_{10}$aryl ($C_2$–$C_6$)alkenyl, $C_6$–$C_{10}$ aryl($C_2$–$C_6$)alkynyl, $C_1$–$C_6$ hydroxyalkyl, nitro, amino, ureido, cyano, $C_1$–$C_6$ acylamino, hydroxy, thiol, $C_1$–$C_6$ acyloxy, azido, $C_1$–$C_6$ alkoxy, or carboxy.

Useful aryl groups are $C_{6-14}$ aryl, especially $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as defined above, as well as cycloalkenyl groups, such as cyclopentenyl, cycloheptenyl and cyclooctenyl.

Useful halo or halogen groups include fluorine, chlorine, bromine and iodine.

Useful arylalkyl groups include any of the above-mentioned $C_{1-10}$ alkyl groups substituted by any of the above-mentioned $C_{6-14}$ aryl groups. Useful values include benzyl, phenethyl and naphthylmethyl.

Useful haloalkyl groups include $C_{1-10}$ alkyl groups substituted by one or more fluorine, chlorine, bromine or iodine atoms, e.g. fluoromethyl, difluoromethyl, trifluoromethyl, pentafluoroethyl, 1,1-difluoroethyl, chloromethyl, chlorofluoromethyl and trichloromethyl groups.

Useful acylamino groups are any $C_{1-6}$ acyl (alkanoyl) attached to an amino nitrogen, e.g. acetamido, propionamido, butanoylamido, pentanoylamido, hexanoylamido as well as aryl-substituted $C_{2-6}$ substituted acyl groups.

Useful acyloxy groups are any $C_{1-6}$ acyl (alkanoyl) attached to an oxy (—O—) group, e.g. formyloxy, acetoxy, propionoyloxy, butanoyloxy, pentanoyloxy, hexanoyloxy and the like.

Useful saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

Useful heteroaryl groups include any one of the following: thienyl, benzo[b]thienyl, naphtho[2,3-b]thienyl, thianthrenyl, furanyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido [1,2-α]pyrimidin-4-one, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g. a pyridyl N-oxide, pyrazinyl N-oxide, pyrimidinyl N-oxide and the like.

Exemplary preferred compounds of the present invention include compounds having polyether substituents. Preferred polyethers for use in the invention include, but are not limited to, optionally substituted polyethyleneglycol, known as PEG. PEGs are water soluble polymers that impart unique physio-chemical properties to compounds and polymers, thus expanding the potential uses of the compounds and polymers. For example, PEG-modified proteins exhibit improved pharmacological performance over non-PEG-modified proteins. See, for example, Delgado, C. et al., Crit. Rev. Ther. Drug Carrier Syst. 9:249–304 (1992). PEG-modified liposomes also exhibit unique properties such as increased permiabilities. Sriwongsitanont, S. and Ueno, M., Chem. Pharm. Bull. 50:1238–1244 (2002). Modifying compounds of the present invention with PEG groups, increases their solubilty thus reducing their systemic toxicity and their toxicity at the site of administration. Particular PEGs for use in the present invention have the formula $-(CH_2CH_2O)_m R_m$ wherein n=1–10 and $R_m$ is hydrogen or $C_{1-10}$ alkyl. Preferred PEGs include, but are not limited to, $HOCH_2CH_2OH$, $CH_3CH_2(OCH_2CH_2)_3OH$, $CH_3(OCH_2CH_2)_4OH$, and $CH_3(CH_2)_7(OCH_2CH_2)_4OH$.

Certain of the compounds of the present invention may exist as stereoisomers including optical isomers. The invention includes all stereoisomers and both the racemic mixtures of such stereoisomers, as well as the individual enantiomers that may be separated according to methods that are well known to those of ordinary skill in the art.

Examples of pharmaceutically acceptable addition salts include inorganic and organic acid addition salts, such as hydrochloride, hydrobromide, phosphate, sulphate, citrate, lactate, tartrate, maleate, fumarate, mandelate and oxalate; and inorganic and organic base addition salts with bases, such as sodium hydroxy, Tris(hydroxymethyl)aminomethane (TRIS, tromethane) and N-methyl-glucamine.

Examples of prodrugs of the compounds of the invention include the simple esters of carboxylic acid containing compounds (e.g. those obtained by condensation with a $C_{1-4}$ alcohol according to methods known in the art); esters of hydroxy containing compounds (e.g. those obtained by condensation with a $C_{1-4}$ carboxylic acid, $C_{3-6}$ dioic acid or anhydride thereof (e.g. succinic and fumaric anhydrides according to methods known in the art); imines of amino containing compounds (e.g. those obtained by condensation with a $C_{1-4}$ aldehyde or ketone according to methods known in the art); and acetals and ketals of alcohol containing compounds (e.g. those obtained by condensation with chloromethyl methyl ether or chloromethyl ethyl ether according to methods known in the art).

The compounds of this invention may be prepared using methods known to those skilled in the art, or the novel methods of this invention. Specifically, gambogic acid can be purified by: (1) preparation of the pyridine salt of the crude extract from gamboge (resin from *Garcinia hanburyi* Hook); (2) repeating recrystallization of the salt in ethanol; and (3) converting the salt to the free acid. Using this procedure, about 10% wt of gambogic acid with purity >99% (HPLC) can be obtained from the crude extract. Gambogic acid and analogs with Formulae I and II also can be separated and purified from gamboge by repeated column chromatography ($SiO_2$, hexane-EtOAc gradient) with the application of a CombiFlash® Sg100 separation system (Isco, Inc. Lincoln, Nebr.).

Derivatives of gambogic acid with Formulae I and II can be prepared as illustrated by exemplary reactions in Scheme 1–2. Reaction of gambogyl piperidine with morpholine produces the morpholinyl addition product of the amide (Scheme 1). Similarly, reaction of gambogyl piperidine with a substituted alcohol, such as N-(2-hydroxyethyl)morpholine in the presence of a base, such as sodium hydride produces the morpholinylethoxy adduct (Scheme 2).

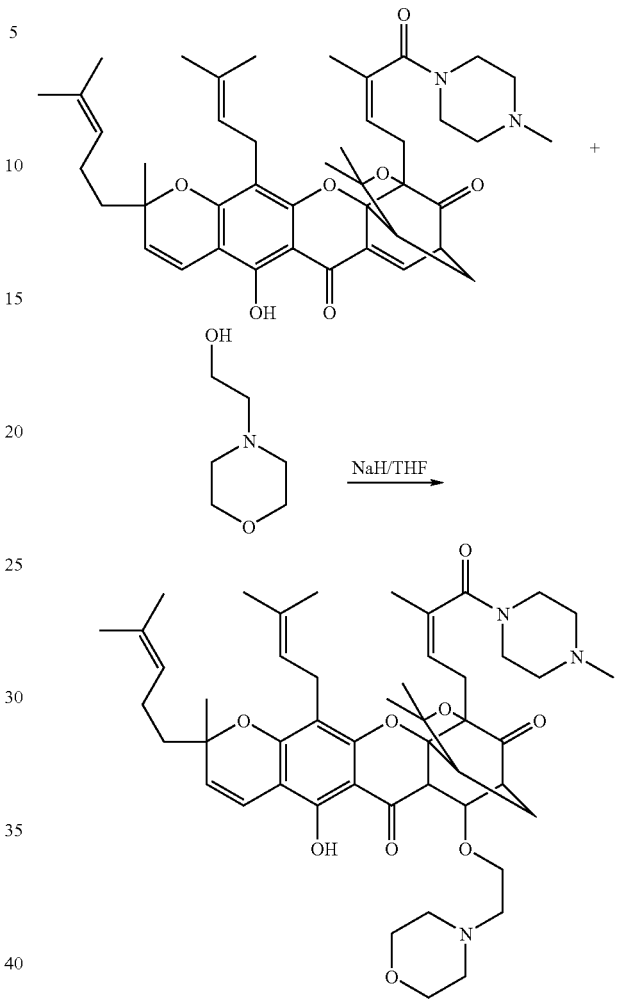

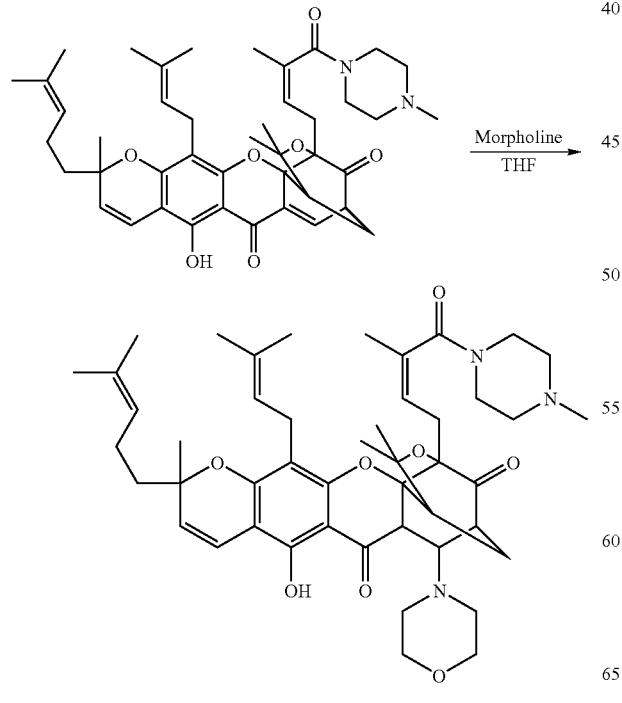

Alternatively, reaction of gambogic acid with an excessive amount of an amine, such as morpholine, in the presence of coupling reagents, such as 1-[3-(dimethylamino)propyl]-3-ethylcarbodiimide hydrochloride (EDC) and 4-(N,N-dimethylamino)pyridine (DMAP), produces the morpholine amide addition product in one step (Scheme 3). Likewise, the reaction of carboxcylic acid derivatives of Formula II with an excess of N-methylpiperazine, under similar conditions, produces the N-methylpiperazine amide addition product in one step (Scheme 4).

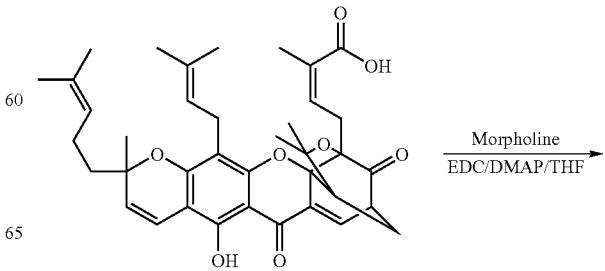

Scheme 5. The reaction of gambogic acid with ethyl iodide in the presence of a base, such as 1,8-diazabicyclo[5.4.0]undec-7-ene (DBU) in a solvent such as N,N-dimethylformamide (DMF), produces the ethyl gambogate product (Scheme 5), which was then used to react with nucleophiles for the preparation of compounds of Formulae I and II.

Derivatives of gambogic acid with Formulae I and II can be prepared as illustrated by the exemplary reaction in An important aspect of the present invention is the discovery that compounds having Formulae I and II are activators of caspases and inducers of apoptosis. Therefore, these compounds are expected to be useful in a variety of clinical conditions in which there is uncontrolled cell growth and spread of abnormal cells, such as in the case of cancer.

Another important aspect of the present invention is the discovery that Michael addition to the double bond in the 9–10 positions to gambogic acid and derivatives, which produces compounds of Formulae I and II, is reversible. For example, methyl 9,10-dihydro-10-morpholinyl-gambogate was found to reverse to methyl gambogate in biological media as shown in Scheme 6. In addition, in the apoptosis inducing and caspase activating assay in cells, methyl 9,10-dihydro-10-morpholinyl-gambogate was found to be active in the 24 h assay but not active in the 5 h assay, indicating that methyl 9,10-dihydro-10-morpholinyl-gambogate is a slow acting compound due to its need to be converted to the methyl gambogate. This reversibility can be exploited to reduce the toxicity of derivatives of gambogic acid and analogs in animals and to make them more suitable as drugs.

Scheme 6

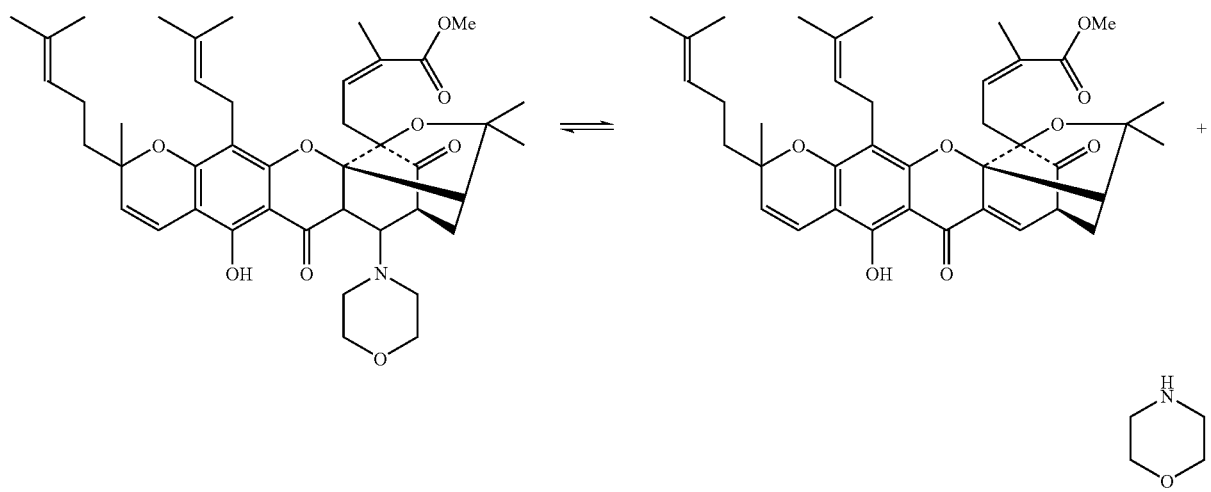

Another important aspect of the present invention, therefore, is the discovery that the compounds defined by the Formulae I–II have unexpectedly reduced toxicity. The compounds described herein cause reduced damage to normal tissue, and hence reduced side effects, at the site of administration. Specific types of tissue damage include, but are not limited to necrosis, decay, eruption, burning, inflammation, irritation, itching, swelling, gastric upset, acid reflux, nausea, vomiting, enteritis and hemorrhoids. Furthermore, the compounds described herein cause reduced or substantially reduced systemic toxicity to tissues and organs such as dermal, vascular, arterial, muscular or fatty tissue, the lining of the mouth, throat, esophagus, stomach, small intestines, large intestines and rectum. The reduced toxicity of compounds of Formulae I–II make it possible to administer these compounds to animals to produce the desirable efficacy. Reduced damage to normal tissue at the site of administration means that multiple administrations can be given at the same site. This is not possible with the non-derivatized compounds which cause severe reactions at the site of administration. Preferably, the compounds can be administered more than once at the same site of administration, more preferably 3, 4, 5, 6, 7, 8, 9, 10, 11, 12, 13, 14, 15, 16, 17, 18, 19 or 20 or more times at the same site of administration.

The phrase "reduced systemic toxicity" as used herein means the compounds of the present invention have a therapeutic index of at least 1.1, preferably at least 1.5. The phrase "substantially reduced systemic toxicity" as used herein means the compounds of the present invention have a therapeutic index of at least 1.5, preferably at least 2.0.

Yet another important aspect of the present invention is the discovery that the compounds described herein are potent and highly efficacious activators of caspases and inducers of apoptosis in drug resistant cancer cells, such as breast and prostate cancer cells, which enables these compounds to kill drug resistant cancer cells. In comparison, most standard anti-cancer drugs are not effective in killing drug resistant cancer cells under the same conditions. Therefore, gambogic acid, its derivatives and analogs, are expected to be useful for the treatment of drug resistant cancer in animals.

The present invention includes a therapeutic method useful to modulate in vivo apoptosis or in vivo neoplastic disease, comprising administering to a subject in need of such treatment an effective amount of a compound, or a pharmaceutically acceptable salt or prodrug of a compound described herein, which functions as a caspase cascade activator and inducer of apoptosis.

The present invention also includes a therapeutic method comprising administering to an animal an effective amount of a compound, or a pharmaceutically acceptable salt or prodrug of said compound of Formulae I and II, wherein said therapeutic method is useful to treat cancer, which is a group of diseases characterized by the uncontrolled growth and spread of abnormal cells. Such diseases include, but are not limited to, Hodgkin's disease, non-Hodgkin's lymphomas, acute and chronic lymphocytic leukemias, multiple myeloma, neuroblastoma, breast carcinomas, ovarian carcinomas, lung carcinomas, Wilms' tumor, cervical carcinomas, testicular carcinomas, soft-tissue sarcomas, chronic lymphocytic leukemia, primary macroglobulinemia, bladder carcinomas, chronic granulocytic leukemia, primary brain carcinomas, malignant melanoma, small-cell lung carcinomas, stomach carcinomas, colon carcinomas, malignant pancreatic insulinoma, malignant carcinoid carcinomas, malignant melanomas, choriocarcinomas, mycosis fungoides, head and neck carcinomas, osteogenic sarcoma, pancreatic carcinomas, acute granulocytic leukemia, hairy cell leukemia, neuroblastoma, rhabdomyosarcoma, Kaposi's sarcoma, genitourinary carcinomas, thyroid carcinomas, esophageal carcinomas, malignant hypercalcemia, cervical hyperplasia, renal cell carcinomas, endometrial carcinomas, polycythemia vera, essential thrombocytosis, adrenal cortex carcinomas, skin cancer, and prostatic carcinomas.

In practicing the therapeutic methods, effective amounts of compositions containing therapeutically effective concentrations of the compounds formulated for oral, intravenous, local and topical application (for the treatment of neoplastic diseases and other diseases in which caspase cascade mediated physiological responses are implicated), are administered to an individual exhibiting the symptoms of one or more of these disorders. The amounts are effective to ameliorate or eliminate one or more symptoms of the disorder. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the disease. Typically, repeated administration is required to achieve the desired amelioration of symptoms.

In another embodiment, a pharmaceutical composition comprising a compound, or a pharmaceutically acceptable salt of a compound described herein, which functions as a caspase cascade activator and inducer of apoptosis in combination with a pharmaceutically acceptable vehicle, is provided.

Another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known cancer chemotherapeutic agent, or a pharmaceutically acceptable salt of said agent. Examples of known anticancer agents which can be used for combination therapy include, but are not limited to alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; and antibodies, such as Herceptin® and Rituxan®. Other known anti-cancer agents, which can be used for combination therapy, include arsenic trioxide, gamcitabine, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine.

In practicing the methods of the present invention, the compound of the invention may be administered together with the at least one known chemotherapeutic agent as part of a unitary pharmaceutical composition. Alternatively, the compound of the invention may be administered apart from the at least one known cancer chemotherapeutic agent. In this embodiment, the compound of the invention and the at least one known cancer chemotherapeutic agent are administered substantially simultaneously, i.e. the compounds are administered at the same time or one after the other, so long as the compounds reach therapeutic levels for a period of time in the blood.

It has been reported that alpha-1-adrenoceptor antagonists, such as doxazosin, terazosin, and tamsulosin can inhibit the growth of prostate cancer cell via induction of apoptosis (Kyprianou, N., et al., *Cancer Res* 60:4550–4555, (2000)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known alpha-1-adrenoceptor antagonists, or a pharmaceutically acceptable salt of said agent. Examples of known alpha-1-adrenoceptor antagonists, which can be used for combination therapy include, but are not limited to, doxazosin, terazosin, and tamsulosin.

It has been reported that sigma-2 receptors are expressed in high densities in a variety of tumor cell types (Vilner, B. J., et al., *Cancer Res*. 55: 408–413 (1995)) and that sigma-2 receptor agonists, such as CB-64D, CB-184 and haloperidol activate a novel apoptotic pathway and potentiate antineoplastic drugs in breast tumor cell lines. (Kyprianou, N., et al., *Cancer Res*. 62:313–322 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known sigma-2 receptor agonists, or a pharmaceutically acceptable salt of said agent. Examples of known sigma-2 receptor agonists, which can be used for combination therapy include, but are not limited to, CB-64D, CB-184 and haloperidol.

It has been reported that combination therapy with lovastatin, a HMG-CoA reductase inhibitor, and butyrate, an inducer of apoptosis in the Lewis lung carcinoma model in mice, showed potentiating antitumor effects (Giermasz, A., et al., *Int. J. Cancer* 97:746–750 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known HMG-CoA reductase inhibitor, or a pharmaceutically acceptable salt of said agent. Examples of known HMG-CoA reductase inhibitors, which can be used for combination therapy include, but are not limited to, lovastatin, simvastatin, pravastatin, fluvastatin, atorvastatin and cerivastatin.

It has been reported that HIV protease inhibitors, such as indinavir or saquinavir, have potent anti-angiogenic activities and promote regression of Kaposi sarcoma (Sgadari, C., et al., *Nat. Med*. 8:225–232 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known HIV protease inhibitor, or a pharmaceutically acceptable salt of said agent. Examples of known HIV protease inhibitors, which can be used for combination therapy include, but are not limited to, amprenavir, abacavir, CGP-73547, CGP-61755, DMP-450, indinavir, nelfinavir, tipranavir, ritonavir, saquinavir, ABT-378, AG 1776, and BMS-232,632.

It has been reported that synthetic retinoids, such as fenretinide (N-(4-hydroxyphenyl)retinamide, 4HPR), have good activity in combination with other chemotherapeutic agents, such as cisplatin, etoposide or paclitaxel in small-cell lung cancer cell lines (Kalemkerian, G. P., et al., *Cancer Chemother. Pharmacol*. 43:145–150 (1999)). 4HPR also was reported to have good activity in combination with gamma-radiation on bladder cancer cell lines (Zou, C., et al., *Int. J. Oncol*. 13:1037–1041 (1998)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known retinoid and synthetic retinoid, or a pharmaceutically acceptable salt of said agent. Examples of known retinoids and synthetic retinoids, which can be used for combination therapy include, but are not limited to, bexarotene, tretinoin, 13-cis-retinoic acid, 9-cis-retinoic acid, α-difluoromethylornithine, ILX23-7553, fenretinide, and N-4-carboxyphenyl retinamide.

It has been reported that proteasome inhibitors, such as lactacystin, exert anti-tumor activity in vivo and in tumor cells in vitro, including those resistant to conventional chemotherapeutic agents. By inhibiting NF-kappaB transcriptional activity, proteasome inhibitors may also prevent angiogenesis and metastasis in vivo and further increase the sensitivity of cancer cells to apoptosis (Almond, J. B., et al., *Leukemia* 16:433–443 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known proteasome inhibitor, or a pharmaceutically acceptable salt of said agent. Examples of known proteasome inhibitors, which can be used for combination therapy include, but are not limited to, lactacystin, MG-132, and PS-341.

It has been reported that tyrosine kinase inhibitors, such as STI571 (Imatinib mesilate, Gleevec®), have potent synergetic effect in combination with other anti-leukemic agents, such as etoposide (Liu, W. M., et al. *Br. J. Cancer* 86:1472–1478 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known tyrosine kinase inhibitor, or a pharmaceutically acceptable salt of said agent. Examples of known tyrosine kinase inhibitors, which can be used for combination therapy include, but are not limited to, Gleevec®, ZD1839 (Iressa®), SH268, genistein, CEP2563, SU6668, SU11248, and EMD121974.

It has been reported that prenyl-protein transferase inhibitors, such as farnesyl protein transferase inhibitor R115777, possess preclinical antitumor activity against human breast cancer (Kelland, L. R., et. al., *Clin. Cancer Res.* 7:3544–3550 (2001)). Synergy of the protein farnesyltransferase inhibitor SCH66336 and cisplatin in human cancer cell lines also has been reported (Adjei, A. A., et al., *Clin. Cancer. Res.* 7:1438–1445 (2001)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known prenyl-protein transferase inhibitor, including farnesyl protein transferase inhibitor, inhibitors of geranylgeranyl-protein transferase type I (GGPTase-I) and geranylgeranyl-protein transferase type-II, or a pharmaceutically acceptable salt of said agent. Examples of known prenylprotein transferase inhibitors, which can be used for combination therapy include, but are not limited to, R115777, SCH66336, L-778,123, BAL9611 and TAN-1813.

It has been reported that cyclin-dependent kinase (CDK) inhibitors, such as flavopiridol, have potent synergetic effect in combination with other anticancer agents, such as CPT-11, a DNA topoisomerase I inhibitor in human colon cancer cells (Motwani, M., et al., *Clin. Cancer Res.* 7:4209–4219, (2001)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known cyclin-dependent kinase inhibitor, or a pharmaceutically acceptable salt of said agent. Examples of known cyclin-dependent kinase inhibitor, which can be used for combination therapy include, but are not limited to, flavopiridol, UCN-01, roscovitine and olomoucine.

It has been reported that in preclinical studies COX-2 inhibitors were found to block angiogenesis, suppress solid tumor metastases, and slow the growth of implanted gastrointestinal cancer cells (Blanke, C. D., *Oncology (Huntingt)* 16(No. 4 Suppl. 3):17–21 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known COX-2 inhibitors, or a pharmaceutically acceptable salt of said agent. Examples of known COX-2 inhibitors, which can be used for combination therapy include, but are not limited to, celecoxib, valecoxib, and rofecoxib.

Another embodiment of the present invention is directed to a composition effective to inhibit neoplasia comprising a bioconjugate of a compound described herein, which functions as a caspase cascade activator and inducer of apoptosis, in bioconjugation with at least one known therapeutically useful antibody, such as Herceptin® or Rituxan®, growth factors, such as DGF, NGF; cytokines, such as IL-2, IL-4, or any molecule that binds to the cell surface. The antibodies and other molecules will deliver a compound described herein to its targets and make it an effective anticancer agent. The bioconjugates could also enhance the anticancer effect of therapeutically useful antibodies, such as Herceptin® or Rituxan®.

Similarly, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound, or a pharmaceutically acceptable salt or prodrug of a compound described herein, which functions as a caspase cascade activator and inducer of apoptosis. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms maintaining immune homeostasis. This deletion of reactive cells has been shown to be regulated by a phenomenon known as apoptosis. Autoimmune diseases have been lately identified as a consequence of deregulated cell death. In certain autoimmune diseases, the immune system directs its powerful cytotoxic effector mechanisms against specialized cells, such as oligodendrocytes in multiple sclerosis, the beta cells of the pancreas in diabetes mellitus, and thyrocytes in Hashimoto's thyroiditis (Ohsako, S., et al., *Cell Death Differ.* 6(1):13–21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly and generalized lymphadenopathy, hypergammaglobulinemia, and autoantibody formation. (Infante, A. J., et al., *J. Pediatr.* 133(5):629–633 (1998) and Vaishnaw, A. K., et al., *J. Clin. Invest.* 103(3):355–363 (1999)). It was reported that overexpression of Bcl-2, which is a member of the Bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al., *Int. J. Mol. Med.* 1(2):475–483 (1998)). It is therefore, evident that many types of autoimmune disease are caused by defects of the apoptotic process and one treatment strategy would be to turn on apoptosis in the lymphocytes that are causing autoimmune disease (O'Reilly, L. A. & Strasser, A., *Inflamm. Res.* 48(1):5–21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., *J. Immunol.* 162(1):603–608 (1999)) reported that by direct injection of DNA expression vectors encoding FasL into the inflamed thyroid, the development of lymphocytic infiltration of the thyroid was inhibited and induction of the death of infiltrating T cells was observed. These results show that FasL expression on thyrocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt-4T cells, both of which were resistant to apoptosis induced by anti-Fas antibody in the absence of bisindolylmaleimide VIII. Potentiation of Fas-mediated apoptosis by bisindolylmaleimide VIII was reported to be selective for activated, rather than non-activated, T cells, and was Fas-dependent. (Zhou, T., et al, *Nat. Med.* 5(1):42–8 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore, the application of a Fas-dependent apoptosis enhancer, such as bisindolylmaleimide VIII, may be therapeutically useful for the more effective elimination of detrimental cells and inhibition of T cell-mediated autoimmune diseases. Therefore, an effective amount of a compound, or a pharmaceutically acceptable salt or prodrug of a compound described herein, which functions as a caspase cascade activator and inducer of apoptosis, should be an effective treatment for autoimmune disease.

Psoriasis is a chronic skin disease, which is characterized by scaly red patches. Psoralen plus ultraviolet A (PUVA) is a widely used and effective treatment for psoriasis vulgaris and Coven, T. R., et al., *Photodermatol. Photoimmunol. Photomed.* 15(1):22–7 (1999), reported that lymphocytes treated with psoralen 8-MOP or TMP plus UVA displayed DNA degradation patterns typical of apoptotic cell death. Ozawa, M., et al., *J. Exp. Med.* 189(4):711–718 (1999) reported that induction of T cell apoptosis could be the main mechanism by which 312-nm UVB resolves psoriasis skin lesions. Low doses of methotrexate may be used to treat psoriasis to restore a clinically normal skin. Heenen, M., et al., *Arch. Dermatol. Res.* 290(5):240–245 (1998), reported that low doses of methotrexate may induce apoptosis and this mode of action could explain the reduction in epidermal hyperplasia during treatment of psoriasis with methotrexate. Therefore, an effective amount of a compound, or a pharmaceutically acceptable salt or prodrug of a compound described herein, which functions as a caspase cascade activator and inducer of apoptosis, should be an effective treatment for psoriasis.

Synovial cell hyperplasia is a characteristic of patients with rheumatoid arthritis (RA). Excessive proliferation of RA synovial cells that, in addition, are defective in synovial cell death might be responsible for the synovial cell hyperplasia. Wakisaka, S., et al., *Clin. Exp. Immunol.* 114(1): 119–28 (1998), found that, although RA synovial cells could die via apoptosis through Fas/FasL pathway, apoptosis of synovial cells was inhibited by proinflammatory cytokines present within the synovium, and suggested that inhibition of apoptosis by the proinflammatory cytokines may contribute to the outgrowth of synovial cells and lead to pannus formation and the destruction of joints in patients with RA. Therefore, an effective amount of a compound, or a pharmaceutically acceptable salt or prodrug of a compound described herein, which functions as a caspase cascade activator and inducer of apoptosis, should be an effective treatment for rheumatoid arthritis.

There has been an accumulation of convincing evidence that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J. Leukoc. Biol.* 61(4): 375–80 (1997)). Boirivant, M., et al., *Gastroenterology* 116(3):557–65 (1999), reported that lamina propria T cells isolated from areas of inflammation in Crohn's disease, ulcerative colitis, and other inflammatory states manifest decreased CD2 pathway-induced apoptosis, and that studies of cells from inflamed Crohn's disease tissue, indicate that this defect is accompanied by elevated Bcl-2 levels. Therefore an effective amount of a compound, or a pharmaceutically acceptable salt or prodrug of a compound described herein, which functions as a caspase cascade activator and inducer of apoptosis, should be an effective treatment for inflammation.

Caspase cascade activators and inducers of apoptosis may also be a desirable therapy in the elimination of pathogens, such as HIV, Hepatitis C and other viral pathogens. The long lasting quiecence, followed by disease progression, may be explained by an anti-apoptotic mechanism of these pathogens leading to persistent cellular reservoirs of the virions. It has been reported that HIV-1infected T leukemia cells or peripheral blood mononuclear cells (PBMCs) underwent enhanced viral replication in the presence of the caspase inhibitor Z-VAD-fmk. Furthermore, Z-VAD-fmk also stimulated endogenous virus production in activated PBMCs derived from HIV-1-infected asymptomatic individuals (Chinnaiyan, A., et al., *Nat. Med.* 3:333 (1997)). Therefore, apoptosis may serve as a beneficial host mechanism to limit the spread of HIV and new therapeutics using caspase/apoptosis activators may be useful to clear viral reservoirs from the infected individuals. Similarly, HCV infection also triggers anti-apoptotic mechanisms to evade the host's immune surveillance leading to viral persistence and hepatocarcinogenesis (Tai, D. I., et al. *Hepatology* 3:656–64 (2000)). Therefore, apoptosis inducers may be useful as therapeutics for HIV and other infectious disease.

Stent implantation has become the new standard angioplasty procedure. However, in-stent restenosis remains the major limitation of coronary stenting. New approaches have been developed to target pharmacological modulation of local vascular biology by local administration of drugs. This allows for drug applications at the precise site and time of vessel injury. Numerous pharmacological agents with antiproliferative properties are currently under clinical investigation, including actinomycin D, rapamycin or paclitaxel coated stents (Regar E., et al., *Br. Med. Bull*. 59:227–248 (2001)). Therefore, apoptosis inducers, which are antiproliferative, may be useful as therapeutics for in-stent restenosis.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 100 mg/kg, or an equivalent amount of the pharmaceutically acceptable salt thereof, per day of the body weight of the mammal being treated for apoptosis-mediated disorders. The compounds may be administered to mammals, e.g. humans, intravenously at a dose of 0.025 to 200 mg/kg, or an equivalent amount of the pharmaceutically acceptable salt thereof, per day of the body weight of the mammal being treated for apoptosis-mediated disorders. Preferably, approximately 0.01 to approximately 50 mg/kg is orally administered to treat or prevent such disorders. For intramuscular injection, the dose is generally approximately one-half of the oral dose. For example, a suitable intramuscular dose would be approximately 0.0025 to approximately 50 mg/kg, and most preferably, from approximately 0.01 to approximately 10 mg/kg. If a known cancer chemotherapeutic agent is also administered, it is administered in an amount which is effective to achieve its intended purpose. The amounts of such known cancer chemotherapeutic agents effective for cancer are well known to those of skill in the art.

The unit oral dose may comprise from approximately 0.01 to approximately 50 mg, preferably approximately 0.1 to approximately 10 mg of the compound of the invention. The unit dose may be administered one or more times daily as one or more tablets, each containing from approximately 0.1 to approximately 10, conveniently approximately 0.25 to 50 mg of the compound or its solvates.

In a topical formulation, the compound may be present at a concentration of approximately 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries, which facilitate processing of the compounds into preparations that can be used pharmaceutically. Preferably, the preparations, particularly those preparations, which can be administered orally and which can be used for the preferred type of administration, such as tablets, dragees, and capsules, and also preparations, which can be administered rectally, such as suppositories, as well as suitable solutions for administration by injection or orally, contain from approximately 0.01 to 99 percent, preferably from approximately 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular apoptosis inducer of the present invention with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular apoptosis inducer of the present invention with a solution of a pharmaceutically acceptable non-toxic base, such as sodium hydroxide, potassium hydroxide, choline hydroxide, sodium carbonate, Tris, N-methyl-glucamine and the like.

The pharmaceutical compositions of the invention may be administered to any animal, which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner, which is itself known, e.g., by means of conventional mixing, granulating, dragee-making, dissolving, or lyophilizing processes. Thus, pharmaceutical preparations for oral use can be obtained by combining the active compounds with solid excipients, optionally grinding the resultant mixture and processing the mixture of granules, after adding suitable auxiliaries, if desired or necessary, to obtain tablets or dragee cores.

Suitable excipients are, in particular: fillers, such as saccharides, e.g. lactose or sucrose, mannitol or sorbitol; cellulose preparations and/or calcium phosphates, e.g. tricalcium phosphate or calcium hydrogen phosphate; as well as binders, such as starch paste, using, e.g. maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g. silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropymethyl-cellulose phthalate, are used. Dye stuffs or pigments may be added to the tablets or dragee coatings, e.g., for identification or in order to characterize combinations of active compound doses.

Other pharmaceutical preparations, which can be used orally, include push-fit capsules made of gelatin, as well as soft, sealed capsules made of gelatin and a plasticizer, such as glycerol or sorbitol. The push-fit capsules can contain the active compounds in the form of granules, which may be mixed with fillers, such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations, which can be used rectally include, e.g. suppositories, which consist of a combination of one or more of the active compounds with a suppository base. Suitable suppository bases are, e.g. natural or synthetic triglycerides, or paraffin hydrocarbons. In addition, it is also possible to use gelatin rectal capsules, which consist of a combination of the active compounds with a base. Possible base materials include, e.g. liquid triglycerides, polyethylene glycols, or paraffin hydrocarbons.

Suitable formulations for parenteral administration include aqueous solutions of the active compounds in water-soluble form, e.g. water-soluble salts and alkaline solutions. In addition, suspensions of the active compounds as appropriate oily injection suspensions may be administered. Suitable lipophilic solvents or vehicles include fatty oils, e.g. sesame oil; or synthetic fatty acid esters, e.g. ethyl oleate or triglycerides or polyethylene glycol-400 (the compounds are soluble in PEG-400). Aqueous injection suspensions may contain substances, which increase the viscosity of the suspension include, e.g. sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments and the like by choice of appropriate carriers.

Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes approximately 40 parts water, approximately 20 parts beeswax, approximately 40 parts mineral oil, and approximately 1 part almond oil.

Ointments may be formulated by mixing a solution of the active ingredient in a vegetable oil, such as almond oil with warm soft paraffin and allowing the mixture to cool. A typical example of such an ointment is one which includes approximately 30% almond oil and approximately 70% white soft paraffin by weight.

Also included within the scope of the present invention are dosage forms of the compounds defined by one of the Formuale I–II, in which the oral pharmaceutical preparations comprise an enteric coating. The term "enteric coating" is used herein to refer to any coating over an oral pharmaceutical dosage form that inhibits dissolution of the active ingredient in acidic media, but dissolves rapidly in neutral to alkaline media and has good stability to long-term storage. Alternatively, the dosage form having an enteric coating may also comprise a water soluble separating layer between the enteric coating and the core.

The core of the enterically coated dosage form comprises a compound defined by one of the Formulae I–II. Optionally, the core also comprises pharmaceutical additives and/or excipients. The separating layer may be a water soluble inert compound or polymer for film coating applications. The separating layer is applied over the core by any conventional coating technique known to one of ordinary skill in the art. Examples of separating layers include, but are not limited to sugars, polyethylene glycol, polyvinylpyrrolidone, polyvinyl alcohol, hydroxypropyl cellulose, polyvinyl acetal diethylaminoacetate and hydroxypropyl methylcellulose. The enteric coating is applied over the separating layer by any conventional coating technique. Examples of enteric coatings include, but are not limited to cellulose acetate phthalate, hydroxypropyl methylcellulose phthalate, polyvinyl acetate phthalate, carboxymethylethylcellulose, copolymers of methacrylic acid and methacrylic acid methyl esters, such as Eudragit®L 12,5 or Eudragit®L 100 (Röhm Pharma), water based dispersions such as Aquateric® (FMC Corporation), Eudragit®L 100-55 (Röhm Pharma) and Coating CE 5142 (BASF), and those containing water soluble plasticizers such as Citroflex® (Pfizer). The final dosage form is either an enteric coated tablet, capsule or pellet.

The following examples are illustrative, but not limiting, of the method and compositions of the present invention. Other suitable modifications and adaptations of the variety of conditions and parameters normally encountered in clinical therapy, and which are obvious to those skilled in the art, are within the spirit and scope of the invention.

EXAMPLE 1

Isolation of Gambogic Acid

Procedure 1:

Step A. The dry gamboge powder (140 g) was extracted with MeOH (3×600 mL) at room temperature for approximately 1 week. The mixture was filtered, and the solvent was removed under reduced pressure to yield a crude extract (122 g) as a yellow powder.

Step B. Gambogic acid pyridine salt. The above crude extract (120 g) was dissolved in pyridine (120 mL), then warm water (30 mL) was added to the stirred solution. After cooling to room temperature, some precipitate was observed. Hexane (120 mL) was added to the mixture, the mixture was filtered, and the solid was washed with hexane and dried. The salt was purified by repeated recrystallization from ethanol and yielded gambogic acid pyridine salt (7.5 g).

Step C. Gambogic acid. The gambogic acid pyridine salt (0.4 g) was dissolved in ether (25 mL) and shaken with aqeuous HCl (1N, 25 mL) for 1 h. The ether solution was then washed with water (2×10 mL), dried and evaporated to yield the title compound (345 mg). $^1$H NMR (CDCl$_3$): 12.66 (s, 1H), 7.43 (d, J=6.9 Hz, 1H), 6.48 (d, J=10.2 Hz, 1H), 5.97 (t, J=7.5 Hz, 1H), 5.26 (d, J=9.9 Hz, 1H), 4.91 (m, 2H), 3.37 (m, 1H), 3.24–2.98 (m, 2H), 2.81 (d, J=6.6 Hz, 1H), 2.41 (d, J=9 Hz, 1H), 2.20 (m, J=8.4, 5.1 Hz, 1H), 1.88 (m, 1H), 1.63 (s, 3H), 1.60 (s, 3H), 1.58 (s, 3H), 1.53 (s, 3H), 1.51 (s, 3H), 1.43 (s, 3H), 1.26 (s, 3H), 1.18 (s, 3H). MS: 627 (M−H).

EXAMPLE 2

Isolation of Gambogenic Acid

The crude extract of gamboge (300 mg) was purified as described in Example 1, procedure 2, to yield 3 mg of gambogenic acid; HPLC: 84%, MS. 629 (M–H).

EXAMPLE 3

Isolation of Gambogenin

The crude extract of gamboge (300 mg) was purified as described in Example 1, procedure 2, to yield 2 mg of gambogenin, HPLC: 71%. MS. 613 (M–H).

EXAMPLE 4

9,10-Dihydro-10-morpholinyl-gambogyl (N-Methylpiperazine)

a) Gambogyl (N-methylpiperazine). A mixture of gambogic acid pyridine salt (4 g, 5.65 mmol), 4-(N,N-dimethylamino)pyridine (137 mg, 1.13 mmol), 1-[3-(dimethylamino)propyl]-3-ethylcarbodiimide hydrochloride (1.41 g, 7.35 mmol) and 1-hydroxybenzotriazole hydrate (762 mg, 5.65 mmol) in anhydrous THF (50 mL) was stirred at room temperature for approximately 0.5 h. To the solution was added N-methyl piperazine (735 mg, 7.35 mmol) and it was stirred at room temperature overnight. The solution was poured into water (50 mL) and was extracted with ethyl acetate (3×50 mL). The combined organic layer was dried over $MgSO_4$ and concentrated to yield the crude product, which was purified by chromatography ($SiO_2$, EtOAc:MeOH gradient, 20:1–7:1) to yield an orange foam (2.68 g, 64%). $^1H$ NMR ($CDCl_3$): 12.85 (s, 1H), 7.52 (d, J=6.6 Hz, 1H), 6.66 (d, J=9.90 Hz, 1H), 5.42 (d, J=10.25 Hz, 1H), 5.05 (m, 2H), 3.62 (m, 1H), 3.40 (m, 2H), 3.28–3.17 (m, 4H), 2.50–1.98 (m, 7H), 2.23 (s, 3H), 1.72 (brs, 6H), 1.63 (brs, 6H), 1.53 (brs, 6H), 1.41 (s, 3H), 1.23 (s, 3H).

b) 9,10-Dihydro-10-morpholinyl-gambogyl (N-methylpiperazine). A solution of gambogyl (N-methylpiperazine) (234 mg, 0.38 mmol) and morpholine (3 mL) in anhydrous THF (15 mL) was stirred at room temperature for approximately 18 h. The solution was concentrated in vacuo. The residue was dissolved in ethyl acetate (50 mL) and washed with brine (3×40 mL), dried over $MgSO_4$, and concentrated in vacuo to yield the title compound as a light yellow solid (245 mg, 81%). $^1H$ NMR ($CDCl_3$): 12.00 (s), 6.68 (d, J=9.9 Hz, 1H), 5.97 (t, J=6.60 Hz, 1H), 5.46 (d, J=10.2 Hz, 1H), 5.18–5.00 (m, 2H), 3.82 (m, 1H), 3.61 (s, 3H), 3.60–3.20 (m, 6H), 2.32 (s, 3H), 1.88 (s, 3H), 1.75 (s, 3H), 1.66 (s, 3H), 1.65 (s, 3H), 1.34 (s, 3H), 1.31 (s, 3H), 1.11 (s, 3H).

EXAMPLE 5

9,10-Dihydro-10-piperidinyl-gambogyl (N-Methylpiperazine)

The title compound was prepared from gambogyl (N-methylpiperazine) and piperidine by a procedure similar to that of Example 4b. $^1H$ NMR ($CDCl_3$): 12.00 (s, 1H), 6.67 (d, J=9.9 Hz, 1H), 6.0 (t, 1H), 5.44 (d, J=10.2 Hz, 1H), 5.47–5.09 (m, 2H), 3.59–3.19 (m, 7H), 2.84–1.16 (m, 51H).

EXAMPLE 6

9,10-Dihydro-10-[2-(morpholinyl)ethylamino]-gambogyl (N-Methylpiperazine)

The title compound was prepared from gambogyl (N-methylpiperazine) and 4-(2-aminoethyl)morpholine by a procedure similar to that of Example 4b. $^1H$ NMR ($CDCl_3$): 12.00 (s, 1H), 6.67 (d, J=9.9 Hz, 1H), 5.97 (t, 1H), 5.46 (d, J=9.9 Hz, 1H), 5.11 (m, 2H), 3.83–3.08 (m, 12H), 2.82–1.12 (m, 48H).

EXAMPLE 7

9,10-Dihydro-10-[4-(2-pyridyl)piperazinyl]-gambogyl (N-Methylpiperazine)

The title compound was prepared from gambogyl (N-methylpiperazine) and 1-(2-pyridyl)piperazine by a procedure similar to that of Example 4b. $^1H$ NMR ($CDCl_3$): 12.00 (s, 1H), 8.11 (s, 1H), 7.4 (t, 1H), 6.67 (m, 3H), 5.97 (t, 1H), 5.46 (d, J=9.9 Hz, 1H), 5.11 (m, 2H), 3.82–3.12 (m, 12H), 2.92–1.13 (m, 44H).

EXAMPLE 8

9,10-Dihydro-10-[2-(morpholinyl)ethoxy]-gambogyl (N-Methylpiperazine)

A mixture of gambogyl (N-methylpiperazine) (0.100 g; 0.140 mmol), N-(2-hydroxyethyl)morpholine (1.4 mL, 14.1 mmol), and sodium hydride (6.7 mg, 0.281 mmol) in anhydrous THF (6 mL) was stirred at room temperature for 18 h. The solution was poured into water (50 mL) and extracted with ethyl acetate (25 mL). The combined organic layers were washed with brine (3×15 mL), dried over $MgSO_4$, and the solvent was removed in vacuo. The crude product was purified by column chromatography (dichloromethane:methanol gradient, 40:1–10:1) to yield an orange oil. $^1H$ NMR ($CDCl_3$): 12.00 (s, 1H), 6.67 (d, J=9.9 Hz, 1H), 5.97 (t, 1H), 5.46 (d, J=9.9 Hz, 1H), 5.11 (m, 2H), 3.98–3.21 (m, 12H), 2.64–1.13 (m, 48H).

EXAMPLE 9

9,10-Dihydro-10-(2-dimethylaminoethoxy)-gambogyl (N-Methylpiperazine)

The title compound was prepared from gambogyl (N-methylpiperazine) and 2-dimethylaminoethanol by a procedure similar to that of Example 8. $^1H$ NMR ($CDCl_3$): 12.00 (s, 1H), 6.67 (d, J=9.9 Hz, 1H), 5.97 (t, 1H), 5.46 (d, J=9.9 Hz, 1H), 5.11 (m, 2H), 3.81–3.28 (m, 12H), 2.81–0.84 (m, 46H).

EXAMPLE 10

9,10-Dihydro-10-morpholinyl-gambogyl Morpholine

A mixture of gambogic acid pyridine salt (2.48 g, 3.5 mmol), morpholine (3 mL, 34.4 mmol), 4-(N,N-dimethylamino) pyridine (85 mg, 0.7 mmol), 1-[3-(dimethylamino)propyl]-3-ethylcarbodiimide hydrochloride (869 mg, 4.55 mmol) in THF (20 mL) was stirred at room temperature for 24 h. The solution was poured into water (50 mL) and was extracted with ethyl acetate (3×50 mL). The combined organic layers were washed with water (3×30 mL), dried, and concentrated to yield the crude product (2.83 g). The crude product was purified by column chromatography to yield the title compound (649 mg, 47%). $^1$H NMR (CDCl$_3$): 12.00 (s, 1H), 6.68 (d, J=9.9 Hz, 1H), 6.00 (t, J=6.60 Hz, 1H), 5.48 (d, J=10.2 Hz, 1H), 5.18–5.00 (m, 2H), 3.82–2.40 (m, 22H), 2.20–1.15 (m, 32H).

EXAMPLE 11

9,10-Dihydro-10-ethoxy-gambogyl Piperidine a) Gambogyl piperidine. The title compound was prepared from gambogic acid pyridine salt (1.50 g, 2.11 mmol) and piperidine (0.209 mL, 2.11 mmol) by a procedure similar to that of Example 4a. $^1$H NMR (CDCl$_3$): 12.85 (s, 1H), 7.56 (d, J=6.6 Hz, 1H), 6.71 (d, J=10.2 Hz, 1H), 5.47 (d, J=9.9 Hz, 1H), 5.1–5.2 (m, 2H), 3.14–3.6 (m, 4H), 2.13–2.51 (m, 5H), 1.28–1.71 (m, 38H).

b) 9,10-Dihydro-10-ethoxy-gambogyl piperidine. The title compound was prepared from gambogyl piperidine and ethanol by a procedure similar to that of Example 8. $^1$H NMR (CDCl$_3$): 12.01 (s, 1H), 6.72 (d, J=6.6 Hz, 1H), 5.97 (s, 1H), 5.52 (d, J=9.9 Hz, 1H), 5.11 (m, 2H), 3.98–3.30 (m, 12H), 1.28–1.71 (m, 41H).

EXAMPLE 12

9,10-Dihydro-10-morpholinyl-gambogyl (Dimethylamine)

a) Gambogyl (dimethylamine). The title compound was prepared from gambogic acid pyridine salt (0.200 g, 0.285 mmol) and dimethylamine (0.141 mL, 0.282 mmol) by a procedure similar to that of Example 4a. $^1$H NMR (CDCl$_3$): 12.95 (s, 1H), 7.52 (d, J=6.9 Hz, 1H), 6.63 (d, J=10.2 Hz, 1H), 5.42 (d, J=9.9 Hz, 1H), 5.32 (m, 1H), 5.04 (m, 2H), 3.24–3.6 (m, 4H), 2.01–2.62 (m, 8H), 1.22–1.61 (m, 30H).

b) 9,10-Dihydro-10-morpholinyl-gambogyl (dimethylamine). The title compound was prepared from gambogyl (dimethylamine) and morpholine by a procedure similar to that of Example 4b. $^1$H NMR (CDCl$_3$): 11.98 (s, 1H), 6.74 (d, J=6.6 Hz, 1H), 5.97 (t, 1H), 5.48 (d, J=9.9 Hz, 1H), 5.15 (m, 2H), 3.69–2.21 (m, 13H), 1.28–1.71 (m, 39H).

EXAMPLE 13

Ethyl 9,10-Dihydro-10-morpholinyl-gambogate a) Ethyl gambogate. A solution of ethyl iodide (31.6 μL, 0.398 mmol) in 0.5 mL of N,N-dimethylformamide was added to a mixture of gambogic acid pyridine salt (0.250 g, 0.398 mmol) and 1,8-diazabicyclo[5.4.0]undec-7-ene (59 μL, 0.398 mmol) in 0.2 mL of N,N-dimethylformamide and the mixture was stirred at room temperature for approximately 3 h. The mixture was poured into brine (30 mL) and was extracted with methylene chloride. The organic layer was washed with brine (2×30 mL), dried over MgSO$_4$ and concentrated to give the crude product, which was purified by column chromatography (EtOAc:hexane, 1:5) to yield 150 mg (90%) of the title compound as an orange solid. $^1$H NMR (CDCl$_3$): 12.95 (s, 1H), 7.6 (d, J=6.6 Hz, 1H), 6.76 (d, J=9.9 Hz, 1H), 6.12 (t, 1H), 5.53 (d, J=9.9 Hz, 2H), 3.01–3.54 (m, 5H), 2.5 (d, J=2.7 Hz, 1H), 2.35 (m, 1H), 2.05 (m, 2H), 1.28–1.72 (m, 33H).

b) Ethyl 9,10-dihydro-10-morpholinyl-gambogate. The title compound was prepared from ethyl gambogate and morpholine by a procedure similar to that of Example 4b. $^1$H NMR (CDCl$_3$): 12.0 (s, 1H), 6.74 (d, J=9.9 Hz, 1H), 6.6 (t, 1H), 5.46 (d, J=5.48 Hz, 1H), 5.15 (m, 2H), 3.71 (m, 4H), 3.4–3.12 (m, 6H), 2.4–2.8 (m, 6H), 1.28–1.98 (m, 35H).

EXAMPLE 14

Methyl 9,10-Dihydro-10-benzyloxy-gambogate a) Methyl gambogate. The title compound was prepared from gambogic acid pyridine salt (0.200 g, 0.318 mmol) and methyl iodide (29.7 μL, 0.318 mmol) by a procedure similar to that of Example 13a. $^1$H NMR (CDCl$_3$): 12.95 (s, 1H), 7.55 (d, J=6.9 Hz, 1H), 6.69 (d, J=10.2 Hz, 1H), 5.95 (t, 1H), 5.45 (d, J=10.2 Hz, 1H), 5.07 (m, 2H), 3.44–2.98 (m, 8H), 1.36–2.55 (m, 31H).

b) Methyl 9,10-dihydro-10-benzyloxy-gambogate. The title compound was prepared from methyl gambogate and benzyl alcohol by a procedure similar to that of Example 8. $^1$H NMR (CDCl$_3$): 12.95 (s, 1H), 7.36 (m, 6H), 6.67 (d, J=9.9 Hz, 1H), 6.58 (t, 1H), 5.48 (d, J=10.2 Hz, 1H), 5.07 (m, 2H), 4.73 (d, J=5.7 Hz, 1H), 3.22–3.60 (m, 6H), 2.51 (d, J=8.1 Hz, 1H), 1.44–2.12 (m, 34H).

EXAMPLE 15

Methyl 9,10-Dihydro-10-(4-acetylpiperazinyl)-gambogate

The title compound was prepared from methyl gambogate and 4-acetylpiperazine by a procedure similar to that of Example 4b. $^1$H NMR (CDCl$_3$): 11.97 (s, 1H), 6.64 (m, 2H), 5.47 (d, J=10.2 Hz, 1H), 5.07 (d, J=27 Hz, 2H), 3.19–3.66 (m, 11H), 2.42–2.76 (m, 4H), 1.16–2.11 (m, 37H).

EXAMPLE 16

Methyl 9,10-Dihydro-10-(piperidinyl)-gambogate

The title compound was prepared from methylgambogate and piperidine by a procedure similar to that of Example 4b. $^1$H NMR (CDCl$_3$): 11.97 (s, 1H), 6.74 (d, J=9.9 Hz, 1H), 5.49 (d, J=10.2 Hz, 1H), 5.02 (m, 2H), 3.67 (m, 3H), 3.26 (m, 4H), 2.81 (m, 3H), 2.35 (m, 5H), 1.25–1.85 (m, 37H).

EXAMPLE 17

9,10-Dihydro-10-[4-(2-pyridyl)piperazinyl]-gambogyl (Diethylamine)

The title compound was prepared from gambogyl (diethylamine) and 1-(2-pyridyl)piperazine by a procedure similar to that of Example 4b. $^1$H NMR (CDCl$_3$): 12.05 (s, 1H), 8.21 (m, 2H), 7.52 (m, 2H), 6.72 (m, 2H), 5.98 (m, 1H), 5.50 (d, J=9.0 Hz, 2H), 5.13 (m, 4H), 3.48 (m, 11H), 2.31–2.85 (m, 9H 1.25–2.21 (m, 32H).

EXAMPLE 18

9,10-Dihydro-10-[4-(2-pyridyl)piperazinyl]-gambogyl (Methylamine)

The title compound was prepared from gambogyl (methylamine) and 1-(2-pyridyl)piperazine by a procedure similar to that of Example 4b. $^1$H NMR (CDCl$_3$): 11.98 (s, 1H), 8.11 (m, 2H), 7.45 (m, 2H), 6.65 (m, 2H), 5.93 (m, 1H), 5.44 (d, J=9.0 Hz, 2H), 5.04 (m, 4H), 4.69 (m, 4H), 2.49–3.42 (m, 9H), 1.23–2.01 (m, 35H).

EXAMPLE 19

9,10-Dihydro-10-(morpholinyl)-gambogyl (Diethylamine)

The title compound was prepared from gambogyl (diethylamine) and morpholine by a procedure similar to that of Example 4b. $^1$H NMR (CDCl$_3$): 12.02 (s, 1H), 6.69 (d, J=9.9 Hz, 1H), 5.92 (m, 1H), 5.46 (d, J=9.2 Hz, 1H), 5.46 (d, J=10.2 Hz, 1H), 5.09 (m, 2H), 3.30–3.61 (m, 13H), 2.46–2.70 (m, 7H), 1.13–1.90 (m, 36H).

EXAMPLE 20

Methyl 9,10-Dihydro-10-ethoxy-gambogate

The title compound was prepared from methyl gambogate and ethanol by a procedure similar to that of Example 8. $^1$H NMR (CDCl$_3$): 11.98 (s, 1H), 6.67 (d, J=9.9 Hz, 1H), 6.58 (m, 1H), 5.12 (d, J=9.9 Hz, 1H), 5.04 (m, 2H) 4.47 (s, 1H), 3.52 (m, 4H), 3.25 (m, 4H), 2.81 (m, 1H), 2.49 (m, 1H), 1.00–2.12 (m, 35H).

EXAMPLE 21

9,10-Dihydro-10-ethoxy-gambogic Acid

The title compound was prepared from gambogic acid and ethanol by a procedure similar to that of Example 8. $^1$H NMR (CDCl$_3$): 11.95 (s, 1H), 6.65 (m, 2H), 5.48 (d, J=10.2 Hz, 1H), 5.11 (m, 2H), 4.46 (s, 2H), 3.17–3.61 (m, 7H), 2.82 (s, 1H), 2.52 (d, J=8.7 Hz, 1H), 1.35–2.07 (m, 33H).

EXAMPLE 22

9,10-Dihydro-10-ethoxy-gambogyl (Diethylamine)

The title compound was prepared from gambogyl (diethylamine) and ethanol by a procedure similar to that of Example 8. $^1$H NMR (CDCl$_3$): 11.98 (s, 1H), 6.66 (d, J=10.8 Hz, 1H), 5.47 (m, 1H), 5.44 (d, J=10.8 Hz, 1H), 5.10 (m, 2H), 4.45 (m, 1H), 3.48–3.58 (m, 3H), 3.20–3.26 (m, 4H), 2.80–2.08 (m, 5H), 1.13–1.96 (m, 36H).

EXAMPLE 23

Ethyl 9,10-Dihydro-10-ethoxy-gambogate

The title compound was prepared from ethyl gambogate and ethanol by a procedure similar to that of Example 8. $^1$H NMR (CDCl$_3$): 12.02 (s, 1H), 6.73 (d, J=10.2 Hz, 1H), 6.61 (m, 1H), 5.52 (d, J=9.9 Hz, 1H), 5.08 (m, 2H), 4.50 (s, 1H), 4.21 (m, 3H), 3.23–4.18 (m, 8H), 2.87 (s, 1H), 2.52 (m, 1H), 1.22–2.13 (m, 34H).

EXAMPLE 24

Methyl 9,10-Dihydro-10-(4-methylpiperazinyl)-gambogate

The title compound was prepared from methyl gambogate and N-methylpiperazine by a procedure similar to that of Example 4b. $^1$H NMR (CDCl$_3$): 12.01 (s, 1H), 6.72 (d, J=9.9 Hz, 2H), 5.51 (d, J=9.6 Hz, 1H), 5.15 (m, 2H), 3.77 (m, 4H), 3.31 (m, 9H), 1.19–2.55 (m, 40H).

EXAMPLE 25

Ethyl 9,10-Dihydro-10-(4-methylpiperazinyl)-gambogate

The title compound was prepared from ethyl gambogate and N-methylpiperazine by a procedure similar to that of Example 4b. $^1$H NMR (CDCl$_3$): 12.06 (s, 1H), 6.71 (m, 2H), 5.51 (d, J=11.1 Hz, 1H), 5.16 (m, 2H), 3.32–3.35 (m, 6H), 1.20–2.84 (m, 48H).

EXAMPLE 26

Ethyl 9,10-Dihydro-10-(4-acetylpiperazinyl)-gambogate

The title compound was prepared from ethyl gambogate and 4-acetylpiperazine by a procedure similar to that of Example 4b. $^1$H NMR (CDCl$_3$): 12.01 (s, 1H), 6.72 (d, J=10.2 Hz, 1H), 6.64 (m, 1H), 5.52 (d, J=10.2 Hz, 1H), 5.15 (m, 2H), 3.23–3.59 (m, 8H), 2.49–2.59 (m, 4H), 1.20–2.13 (m, 42H).

EXAMPLE 27

Ethyl 9,10-Dihydro-10-(piperidinyl)-gambogate

The title compound was prepared from ethyl gambogate and piperidine by a procedure similar to that of Example 4b. $^1$H NMR (CDCl$_3$): 11.90 (s, 1H), 6.51 (m, 2H), 5.34 (d, J=10.2 Hz, 1H), 4.97 (m, 2H), 4.06 (m, 2H), 3.06–3.12 (m, 5H), 2.68 (m, 2H), 1.83–2.42 (m, 5H), 1.00–1.61 (m, 39H).

EXAMPLE 28

2-{2-[2-(2-Octyloxyethoxy)ethoxy]ethoxy}ethyl Gambogate a) 2-{2-[2-(2-Octyloxyethoxy)ethoxy]ethoxy}ethyl toluene-4-sulfonate. To a solution of 2-{2-[2-(2-octyloxyethoxy)ethoxy]ethoxy}ethanol (615 mg, 2.34 mmol), N,N-dimethylpyridine (12 mg, 0.1 mmol) and triethylamine (0.83 mL) in dichloromethane (10 mL) was added p-toluenesulfonyl chloride (410 mg, 2.15 mmol). The solution was stirred at room temperature for 19 h. The reaction mixture was diluted with EtOAc (50 mL), washed with saturated NaHCO$_3$ (10 mL), brine (10 mL) and dried over MgSO$_4$. The solvent was evaporated and the crude was purified by column chromatography (SiO$_2$, EtOAc:hexanes) to give a clear thick oil (634 mg, 71%). $^1$H NMR (CDCl$_3$): 7.80 (m, 2H), 7.34 (d, J=7.8 Hz, 2H), 4.15 (m, 2H), 3.68 (m, 2H), 3.65–3.55 (m, 12H), 3.44 (t, J=6.9 Hz, 2H), 2.44 (s, 3H), 1.57 (m, 2H), 1.27 (m, 10 H), 0.88 (t, J=6.9 Hz, 3H).

b) 2-{2-[2-(2-Octyloxyethoxy)ethoxy]ethoxy}ethyl gambogate. A mixture of gambogic acid (630 mg, 1.00 mmol), 2-{2-[2-(2-octyloxyethoxy)ethoxy]ethoxy}ethyl toluene-4-sulfonate (634 mg, 1.38 mmol), sodium iodide (340 mg, 2.27 mmol), and potassium carbonate (280 mg, 2.03 mmol) in dry acetone (25 mL) was stirred at 50° C. under Argon for 24 h. The solvent was evaporated and the residue was mixed with EtOAc (50 mL). It was washed with water (2×10 mL), brine (10 mL), dried over MgSO$_4$, and evaporated to give a dark brown residue. The crude product was purified by column chromatography (SiO$_2$, EtOAc:hexanes/25–50%) to give a light yellow oil (398 mg, 43%). $^1$H NMR (CDCl$_3$): 12.84 (s, 1H), 7.53 (d, J=7.2 Hz, 1H), 6.66 (d, J=10.2 Hz, 1H), 6.01 (m 1H), 5.43 (d, J=9.9 Hz, 1H), 5.05 (m 2H), 3.98

(m, 2H), 3.67–3.52 (m, 14H), 3.47 (m, 1H), 3.44 (t, J=6.6 Hz, 2H), 3.30 (dd, J=8.1, 14.7 Hz, 1H), 3.20–2.90 (m, 3H), 2.51 (d, J=9.3 Hz, 1H), 2.31 (dd, J=4.8, 13.2 Hz, 1H), 2.02 (m, 2H), 1.78 (m, 1H), 1.73 (s, 3H), 1.69 (s, 6H), 1.65 (s, 3H), 1.64 (s, 3H), 1.60 (m, 1H), 1.55 (s, 3H), 1.44 (s, 3H), 1.38 (dd, J=8.2, 12.0 Hz, 1H), 1.28 (m, 15H), 0.88 (t, J=6.9 Hz, 3H).

EXAMPLE 29

2-{2-[2-(2-Octyloxyethoxy)ethoxy]ethoxy}ethyl 9,10-Dihydro-10-morpholinyl gambogate To a solution of 2-{2-[2-(2-octyloxyethoxy)ethoxy]ethoxy}ethyl gambogate (274 mg, 0.30 mmol) in dichloromethane (10 mL) was added morpholine (80 mg, 0.92 mmol) under Argon at room temperature. The solution was stirred overnight. Thin layer chromatographic (TLC) analysis showed the presence of starting material. Additional morpholine (180 mg, 2.06 mmol) was added and the solution was stirred for 1 h. The solvent was evaporated and the crude product was purified by column chromatography (SiO$_2$, EtOAc:hexanes 10–50%) to give the product as a clear oil (254 mg, 85%). $^1$H NMR (CDCl$_3$): 11.97 (s, 1H), 6.66 (d, J=9.9 Hz, 1H), 6.62 (m, 1H), 5.45 (d, J=10.2 Hz, 1H), 5.09 (m, 1H), 5.01 (m, 1H), 4.21 (dd, J=4.8, 6.0 Hz, 2H), 3.69 (t, J=5.1 Hz, 2H), 3.65–3.55 (m, 15H), 3.44 (t, J=6.9 Hz, 2H), 3.33–3.10 (m, 6H), 2.80 (dd, J=4.2, 5.7 Hz, 1H), 2.6–2.4 (m, 4H), 2.08 (m, 2H), 2.00–1.93 (m, 4H), 1.78 (m, 1H), 1.74 (s, 3H), 1.66 (s, 3H), 1.63 (s, 3H), 1.58 (s, 3H), 1.57 (s, 3H), 1.50 (m, 1H), 1.36 (s, 3H), 1.34 (s, 3H), 1.27 (m, 12H), 1.14 (s, 3H), 0.88 (t, J=6.9 Hz, 3H).

EXAMPLE 30

2-[2-(2-Ethoxyethoxy)ethoxy]ethyl Gambogate a) 2-[2-(2-Ethoxyethoxy)ethoxy]ethyl toluene-4-sulfonate. The title compound was prepared from 2-[2-(2-methoxyethoxy)ethoxy]ethanol (358 mg, 2.0 mmol) and p-toluenesulfonyl chloride (400 mg, 2.1 mmol) by a procedure similar to Example 28(a) as a clear thick oil (507 mg, 73%). $^1$H NMR (CDCl$_3$): 7.79 (d, J=8.4 Hz, 2H), 7.34 (d, J=8.4 Hz, 2H), 4.26 (m, 2H), 3.68 (m 2H), 3.63–3.48 (m, 10H), 2.44 (s, 3H), 1.20 (dt, J=0.9, 8.0 Hz, 3H).

b) 2-[2-(2-Ethoxyethoxy)ethoxy]ethyl gambogate. The title compound was prepared from gambogic acid (126 mg, 0.20 mmol) and 2-[2-(2-ethoxyethoxy)ethoxy]ethyl toluene-4-sulfonate (68 mg, 0.20 mmol) by a procedure similar to Example 28(b) as a light yellow oil (76 mg, 48%). $^1$H NMR (CDCl$_3$): 12.84 (s, 1H), 7.54 (d, J=6.9 Hz, 1H), 6.66 (d, J=10.2 Hz, 1H), 6.01 (dt, J=1.2, 7.2 Hz, 1H), 5.43 (d, J=10.2 Hz, 1H), 5.04 (m, 2H), 3.97 (m, 2H), 3.64–3.46 (m, 13H), 3.31 (dd, J=8.1, 14.7 Hz, 1H), 3.20–2.90 (m, 3H), 2.51 (d, J=9.3 Hz, 1H), 2.31 (dd, J=4.8, 13.2 Hz, 1H), 2.02 (m, 2H), 1.78 (m,1H), 1.73 (s, 3H), 1.69 (s, 6H), 1.65 (s, 3H), 1.64 (s, 3H), 1.60 (m, 1H), 1.55 (s, 3H), 1.44 (s, 3H), 1.38 (dd, J=8.2, 12.0 Hz, 1H), 1.28 (s, 3H), 1.20 (t, 6.9 Hz, 3H).

EXAMPLE 31

2-[2-(2-Ethoxyethoxy)ethoxy]ethyl 9,10-Dihydro-10-morpholinyl gambogate

The title compound was prepared from 2-[2-(2-ethoxyethoxy)ethoxy]ethyl gambogate (59 mg, 0.0745 mmol) and morpholine (65 mg, 0.75 mmol) by a procedure similar to Example 29 as a clear oil (35 mg, 54%). $^1$H NMR (CDCl$_3$): 11.97 (s, 1H), 6.65 (d, J=9.9 Hz, 1H), 6.1 (m, 1H), 5.45 (d, J=10.2 Hz 1H), 5.09 (m, 1H), 5.01 (m, 1H), 4.21 (t, J=4.9 Hz, 2H), 3.69 (t, J=5.1 Hz, 2H), 3.64–3.55 (m, 11H), 3.51 (q, 6.9 Hz, 2H), 3.40–3.12 (m, 6H), 2.75 (m, 1H), 2.56 (m, 4H), 2.08 (dd, J=8.4, 10.5 Hz, 2H), 1.96 (m, 4H), 1.77 (m, 1H), 1.73 (s, 3H), 1.66 (s, 3H), 1.63 (s, 3H), 1.58 (s, 3H), 1.56 (s, 3H), 1.49 (m, 1H), 1.36 (s, 3H), 1.34 (s, 3H), 1.96 (t, J=7.2 Hz, 3H), 1.13 (s, 3H).

EXAMPLE 32

Propyl Gambogate

The title compound was prepared in about 73% yield from gambogic acid and propyliodide by a procedure similar to that of Example 13(a). $^1$H NMR (CDCl$_3$): 12.84 (s, 1H), 7.53 (d, J=6.6 Hz, 1H), 6.67 (d, J=10.2 Hz, 1H), 6.01 (t, J=7.2 Hz, 1H), 5.42 (d, J=10.2 Hz, 1H), 5.07–5.02 (m, 2H), 3.79 (m, 2H), 3.47 (m, 1H), 3.38–3.20 (m, 2H), 3.18–2.80 (m, 2H), 2.51 (d, J=9.00 Hz, 1H), 2.34–2.28 (m, 1H), 2.10–1.95 (m, 1H), 1.78(s, 3H), 1.69 (s, 6H), 1.65 (s, 3H), 1.64 (s, 3H), 1.52 (m, 3H), 1.42 (s, 3H), 1.31 (S, 3H), 1.28 (s, 3H), 1.24 (s, 3H), 0.88 (s, 3H).

EXAMPLE 33

Propyl 9,10-Dihydro-10-morpholinyl-gambogate

The title compound was prepared in about 85% yield from propyl gambogate and morpholine by a procedure similar to that of Example 13(b). $^1$H NMR (CDCl$_3$): 11.98 (s, 3H), 6.66 (d, J=9.90 Hz, 1H), 6.60 (t, J=6.6 Hz, 1H), 5.45 (d, J=10.2 Hz, 1H), 5.09 (m, 1H), 5.01 (m, 1H), 4.03 (t, J=6.6 Hz, 2H), 3.70–3.50 (m, 4H), 3.40–3.10 (m, 5H), 2.78 (m, 1H), 2.60–2.40 (m, 5H), 1.95 (s, 3H), 1.74 (s, 3H), 1.66 (s, 3H), 1.63 (s, 3H), 1.57 (s, 3H), 1.36 (s, 3H), 1.35 (s, 3H), 1.14 (s, 3H), 0.93 (t, J=6.90 Hz, 3H).

EXAMPLE 34

2-{2-[2-(2-Methoxyethoxy)ethoxy]ethoxy}ethyl gambogate

A mixture of gambogic acid (251.2 mg, 0.4 mmol), 1-chloro-2-{2-[2-(2-methoxyethoxy)ethoxy]ethoxy }ethane (127.2 mg, 0.4 mmol) and potassium carbonate (80 mg, 0.57 mmol) in acetone (15 mL) was stirred at 50 ° C. for 16 h. It was evaporated to dryness and the residue was diluted with water (40 mL) and extracted with ethyl acetate (3×20 mL). The organic layer was dried, concentrated and the residue was purified by column chromatography (SiO$_2$, CH$_2$Cl$_2$/MeOH=50:1) to give about 157 mg (48%) of the title compound. $^1$H NMR (CDCl$_3$): 12.85 (s, 1H), 7.54 (d, J=6.9Hz, 1H), 6.66 (d, J=10.2 Hz, 1H), 6.01 (t, J=6.9 Hz, 1H), 5.43 (d, J=10.5Hz, 1H), 5.05 (m, 2H), 3.98 (m, 2H), 3.75–3.45 (m, 16H), 3.38 (s, 3H), 2.51 (d, J=9 Hz, 1H), 2.31 (m, 1H), 1.74 (s, 3H), 1.69 (bs, 6H), 1.64 (s, 3H), 1.62 (s, 3H), 1.59 (s, 6H), 1.55 (s, 3H), 1.44 (s, 3H), 1.26 (s, 3H).

EXAMPLE 35

2-{2-[2-(2-Methoxyethoxy)ethoxy]ethoxy}ethyl 9,10-Dihydro-10-morpholinyl-gambogate The title compound was prepared in about 84% yield from 2-{2-[2-(2-methoxy-ethoxy)ethoxy]ethoxy}ethoxy gambogate and morpholine by a procedure similar to that of Example 13(b). $^1$H NMR (CDCl$_3$): 11.91(s), 6.58 (d, J=9.9 Hz, 1H), 6.55 (t, J=6.60 Hz, 1H), 5.40 (d, J=9.9 Hz, 1H), 5.05 (m, 1H), 4.92 (m, 1H), 4.18 (m, 2H), 3.70–3.45 (m, 14H), 3.30 (s, 3H), 1.90 (s, 3H), 1.68 (s, 3H), 1.60 (s, 3H), 1.50 (s, 3H), 1.38 (s, 3H), 1.30 (s, 3H), 1.08 (s, 3H).

EXAMPLE 36

2-Hydroxyethyl Gambogate

The title compound was prepared in about 41% yield from gambogic acid and 2-iodoethanol by a procedure similar to that of Example 13(a). $^1$H NMR (CDCl$_3$): 12.86 (s, 1H), 7.54 (d, J=6.9 Hz, 1H), 6.68 (d, J=9.9 Hz, 1H), 6.00 (t, J=7.5 Hz, 1H), 5.46 (d, J=9.9 Hz, 1H), 5.07–5.02 (m, 2H), 3.79 (m, 2H), 3.47 (m, 1H), 3.38–3.20 (m, 2H), 3.18–2.80 (m, 2H), 2.51 (d, J=9.00 Hz, 1H), 4.20–3.90 (m, 2H), 3.70 (q, 2H), 3.48 (m, 1H), 3.40–3.20 (m, 2H), 2.98 (d, J=8.1 Hz, 1H), 2.53 (d, J=9.60 Hz, 1H), 2.34–2.28 (q, 1H), 2.10 (t, J=6.60 Hz, 1H), 2.05–1.95 (m, 2H), 1.74 (s, 3H), 1.72 (s, 3H), 1.69 (s, H), 1.65 (bs, 6H), 1.53 (s, 3H), 1.45 (s, 3H), 1.29 (s, 3H).

EXAMPLE 37

2-Hydroxyethyl 9,10-Dihydro-10-morpholinyl-gambogate

The title compound was prepared in about 65% yield from (2-hydroxyethyl) gambogate and morpholine by a procedure similar to that of Example 13(b). $^1$H NMR (CDCl$_3$): 11.96 (s, 1H), 6.66 (d, J=9.90 Hz, 1H), 6.59 (t, J=7.5 Hz, 1H), 5.46 (d, J=9.90 Hz, 1H), 5.09 (t, J=7.20 Hz, 1H), 5.01 (t, J=7.20 Hz, 1H), 4.34–4.18 (m, 2H), 3.88–3.80 (m, 2H), 3.70–3.55 (m, 4H), 2.78 (m, H), 2.60–2.38 (m, 5H), 2.31 (t, J=6.60 Hz, 1H), 2.18–1.90 (m, 5H), 1.74 (s, 3H), 1.66 (s, 3H), 1.64 (s, 3H), 1.57 (s, 3H), 1.55 (s, 3H), 1.35 (s, 3H), 1.33 (s, 3H), 1.13 (s, 3H).

EXAMPLE 38

Methyl 9,10-Dihydro-gambogate and Methyl 9,10,12-Trihydro-12-hydroxygambogate To a solution of methyl gambogate (1 g, 1.59 mmol) in dichloromethane (30 mL) was added L-selectride in THF (2.5 mL, 2.5 mmol) at −78° C. The solution was stirred at −78° C. for 5 min, allowed to warm to room temperature, and stirred for 30 min. The reaction was quenched with icewater (30 ml) and neutralized with about 2N aqueous hydrochloride (10 mL). The organic layer was washed with water (3×20 mL), dried over Na$_2$SO$_4$ and concentrated in vacuo. The residue was purified by column chromatography (SiO$_2$, Hexane/EtOAc 10:1) to give about 201 mg of methyl 9,10-dihydro-gambogate (20%). $^1$H NMR (CDCl$_3$): 11.95 (s, 1H), 6.66 (d, J=9.90 Hz, 1H), 6.46 (t, J=7.20 Hz, 1H), 5.45 (d, J=9.90 Hz, 1H), 5.10 (m, 1H), 5.04 (m, 1H), 3.68 (s, 3H), 3.36–3.12 (m, 5H), 2.84 (m, 1H), 2.58 (d, J=9.90 Hz, 1H), 2.42 (bs, 1H), 1.84 (s, 3H), 1.76 (s, 3H), 1.66 (s, 3H), 1.64 (s, 3H), 1.59 (s, 3H), 1.36 (s, 3H), 1.34 (s, 3H), 1.13 (s, 3H); and about 10 mg of methyl 9,10-dihydro-12-hydroxy-gambogate (1%) as solid. $^1$H NMR (CDCl$_3$): 12.03 (s, 1H), 6.66 (d, J=9.90 Hz, 1H), 6.28 (t, J=7.20 Hz, 1H), 5.35 (d, J=9.90 Hz, 1H), 5.12–5.08 (m, 2H), 3.72 (s, 3H), 3.66 (d, J=5.70 Hz, 1H), 3.34–3.18 (m, 5H), 2.50 (m, 1H), 2.31 (d, J=9.60 Hz, 1H), 2.07 (m, 2H), 1.84 (s, 3H), 1.96 (s, 3H), 1.73 (s, 3H), 1.66 (s, 3H), 1.65 (s, 3H), 1.56 (s, 3H), 1.40 (s, 3H) 1.38 (s, 3H), 1.36 (s, 3H).

EXAMPLE 39

Methyl 32,33-Epoxy-37,38-epoxy-gambogate and Methyl 37,38-Epoxy gambogate

To a solution of methyl gambogate (256.8 mg, 0.4 mmol) in dichloromethane (15 mL) was added 3-chloroperoxybenzoic acid (98.57 mg, 70% purity, 0.4 mmol). The solution was stirred at room temperature for 30 min, concentrated in vacuo, and the residue was purified by column chromatography (SiO$_2$, Hexane/EtOAc 8:1) to give about 88 mg of methyl 32,33-epoxy-37,38-epoxy-gambogate (33%). $^1$H NMR (CDCl$_3$): 12.90 and 12.84 (s, 1H), 7.58–7.54 (m, 1H), 6.74–6.68 (m, 1H), 6.02–5.78 (m, 1 H), 5.48–5.42 (m, 1H), 3.50 (t, J=4.2 Hz, 1H), 3.43 and 3.42 (s, 3H), 3.20–2.80 (m, 5H), 2.54 (t, J=10.2 Hz, 1H), 2.32 (q, J=14.1, 4.8 Hz, 1H), 1.77 (s, 3H), 1.76 (s, 3H), 1.66 (bs, 6H), 1.48 (s, 3H), 1.42 (s, 3H), 1.30 (s, 3H), 1.25 and 1.24 (s, 3H); and about 112 mg of (42%) methyl 37,38-epoxy-gambogate as a solid. $^1$H NMR (CDCl$_3$): 12.95 and 12.92 (s, 1H), 7.58–7.53 (m, 1H), 6.71–6.69 (m, 1H), 6.02–5.90 (m, 1H), 5.50–5.40 (m, 1H), 5.06–4.98 (m, 1H), 3.49 (m, 1H), 3.43 (s, 3H), 3.38–3.10 (m,1H), 2.99 (t, J=6.30 Hz, 1H), 2.53 (d, J=9.30 Hz, 1H), 2.32 (q, J=14.1, 4.8 Hz, 1H), 1.74 (s, 3H), 1.69 (s, 3H), 1.67 (s, 3H), 1.65 (s, 3H), 1.49 (s, 3H), 1.29 (s, 3H), 1.28 (s, 3H), 1.23 and 1.204 (s, 3H).

EXAMPLE 40

Methyl 9,10-Epoxy-gambogate

To a mixture of methyl gambogate (193 mg, 0.3 mmol) and potassium carbonate hydrate (495.7 mg, 3 mmol) in dichloromethane (10 ml) was added hydrogen peroxide (102 mg, 3 mmol). The reaction was stirred at room temperature overnight, diluted with ethyl acetate (35 ml) and washed with brine (3×50 ml). The organic layer was dried over Na$_2$SO$_4$, concentrated in vacuo, and the residue was purified by column chromatography (SiO$_2$, Hexane/EtOAc=3:1) to give the title compound (134 mg, 68%). $^1$H NMR (CDCl$_3$): 12.21 (s, 1H), 6.66 (d, J=10.5 Hz, 1H), 6.54 (t, J=6.30 Hz, 1H), 5.48 (d, J=10.2 Hz, 1H), 5.09 (t, J=7.20 Hz, 1H), 4.99 (t, J=6.60 Hz, 1H) 4.31 (d, J=4.80 Hz, 1H), 3.64 (s, 3H), 3.28 (t, J=6.90 Hz, 2H), 3.19 (d, J=6.30 Hz, 2H), 3.08 (t, J=4.20 Hz, 1H), 2.54 (d, J=8.70 Hz, 1H), 2.18 (q, J=14.1, 4.8 Hz, 1H), 2.09 (s, 2H), 1.93 (s, 3H), 1.73 (s, 3H), 1.69 (s, 3H), 1.66 (s, 3H), 1.64 (s, 3H), 1.54 (s, 3H), 1.41 (s, 3H), 1.21 (s, 3H).

EXAMPLE 41

Butyl Gambogate

The title compound was prepared in about 64% yield from gambogic acid and butyliodide by a procedure similar to that of Example 13(a). $^1$H NMR (CDCl$_3$): 12.85 (s, 1H), 7.53 (d, J=6.9 Hz, 1H), 6.67 (d, J=10.2 Hz, 1H), 6.01 (t, J=7.8 Hz, 1H), 5.43 (d, J=10.2 Hz, 1H), 5.05 (brs, 2H), 3.90–3.79 (m, 2H), 3.49–3.45 (m, 1H), 3.36–3.28 (m, 1H), 3.19–2.95 (m, 3H), 2.52 (d, J=9.30 Hz, 1H), 2.34–2.28 (m, 1H), 2.05–1.20 (m, 33H), 0.96–0.85 (m, 3H).

EXAMPLE 42

Isobutyl Gambogate

The title compound was prepared in about 46% yield from gambogic acid and 2-methylpropyliodide by a procedure similar to that of Example 13(a). $^1$H NMR (CDCl$_3$): 12.85 (s, 1H), 7.53 (d, J=6.9 Hz, 1H), 6.66 (d, J=10.2 Hz, 1H), 6.03 (t, J=7.2 Hz, 1H), 5.43 (d, J=9.90 Hz, 1H), 5.08–5.03 (m, 2H), 3.69–3.56 (m, 2H), 3.49–3.45 (m, 1H), 3.35–3.28 (m, 1H), 3.21–3.14 (m, 1H), 3.02–2.97 (m, 2H), 2.52 (d, J=9.60 Hz, 1H), 2.34–2.28 (m, 1H), 2.07–2.00 (m, 2H), 1.83–1.26 (m, 28H), 0.82–0.80 (m, 6H).

EXAMPLE 43

Butyl 9,10-Dihydro-10-morpholinyl-gambogate

The title compound was prepared in about 22% yield from butyl gambogate and morpholine by a procedure similar to that of Example 13(b). $^1$H NMR (CDCl$_3$): 11.98 (s, 1H), 6.68–6.60 (m, 2H), 5.45 (d, J=10.5 Hz, 1H), 5.10–5.02 (m, 2H), 4.13–4.05 (m, 2H), 3.65–3.58 (m, 4H), 3.33–3.17 (m, 6H), 2.79–2.75 (m, 1H), 2.53–2.46 (m, 4H), 2.10–2.05 (m, 2H), 2.01–1.95 (m, 4H), 1.78–1.24 (m, 26H), 1.14 (s, 3H), 0.90 (t, J=7.20 Hz, 3H).

EXAMPLE 44

Isobutyl 9,10-Dihydro-10-morpholinyl-gambogate

The title compound was prepared in about 25% yield from isobutyl gambogate and morpholine by a procedure similar to that of Example 13(b). $^1$H NMR (CDCl$_3$): 11.98 (s, 1H), 6.68–6.59 (m, 2H), 5.45 (d, J=9.90 Hz, 1H), 5.10–5.02 (m, 2H), 3.86–3.84 (m, 2H), 3.67–3.55 (m, 4H), 3.36–3.15 (m, 6H), 2.77 (t, J=4.8 Hz, 1H), 2.54–2.46 (m, 4H), 2.13–1.23 (m, 29H), 1.14 (s, 3H), 0.94–0.91 (m, 6H).

EXAMPLE 45

3,4,9,10,32,33,37,38-Octahydro-gambogic Acid

A solution of gambogic acid (35 mg, 0.056 mmol) in 4 mL of ethanol was hydrogenated over Pd on carbon at 1 atm H$_2$ pressure for 2 h. The reaction mixture was filtered, concentrated in vacuo, and the residue was purified by chromatography (SiO$_2$, 30% ethyl acetate/hexanes) to give the title compound (35 mg, 0.056 mmol, 100%). $^1$H NMR (CDCl$_3$): 6.18 (m, 1H), 3.42 (m, 1H), 3.17 (m, 1H), 2.87 (m, 2H), 1.83–2.52 (m, 3H), 2.41–2.64 (m, 5H), 1.71 (s 3H), 1.73–1.78 (m, 2H), 1.51–1.38 (m, 5H), 1.10–1.38 (m, 10H), 0.93 (s, 3H), 0.91 (s, 3H), 0.88 (d, 6H, J=6.6), 0.87 (d, 6H, J=6.6). MS: [M−H]$^-$=637, [M+H]$^+$=639.

EXAMPLE 46

Ethyl 3,4,9,10,32,33,37,38-Octahydro-10-morpholinyl-gambogate

A solution of ethyl 9,10-dihydro-10-morpholinyl-gambogate was hydrogenated as described in Example 45 and the crude product was purified by chromatography (SiO$_2$, 15% ethyl acetate/hexanes) to give the title compound (100%). 1H NMR (CDCl$_3$): 6.62 (m, 1H), 5.06 (m, 1H), 4.12 (q, J=7.2, 2H), 3.60 (m, 4H), 3.30 (m, 4H), 2.42–2.61 (m, 8H), 1.71–2.05 (m, 8H), 1.11–1.66 (m, 27H), 0.93 (dd, J=6.3, 4.5, 3H), 0.87 (d, J=6.6, 6H).

EXAMPLE 47

Ethyl 3,4,32,33,37,38-Hexahydro-gambogate

To a solution of ethyl 3,4,9,10,32,33,37,38-octahydro-10-morpholinyl-gambogate (12.3 mg, 0.016 mmol) in chloroform was added glacial acetic acid (60 uL) and the mixture was stirred for two days. The solvents were evaporated under vaccum and the residue was purified by chromatography (SiO$_2$, 12% ethyl acetate/hexanes) to give the title compound (10 mg, 0.015 mmol, 92%). $^1$H NMR (CDCl$_3$): 7.53 (d, J=6.9, 1H), 6.05 (t, J=4.8, 1H), 5.04 (m, 1H), 3.89 (q, J=6.3, 2H), 3.45 (m, 1H), 3.13–3.35 (m, 1H), 2.84–3.03 (m, 1H), 2.45–2.69 (m, 4H), 2.30 (dd, J=13.5, 4.5, 1H), 1.07–1.71 (m, 33H), 0.08–0.96 (m, 10H). MS: [M−H]$^-$=662, [M+H]$^+$=664.

EXAMPLE 48

Ethyl 12-Hydro-12-hydroxy-gambogate

To a solution of anhydrous cerium chloride (26 mg, 0.105 mmol) in 6 mL of absolute methanol was added 1 mL of dry THF and ethyl gambogate (58 mg, 0.090 mmol) and the mixture was cooled to −50° C. To this mixture was added NaBH$_4$ portion wise (5×10 mg) over 1 hr and the reaction was quenched by adding about 200 uL of about 1N HCl. The mixture was allowed to warm to room temperature and most of the solvents were removed under vacuum. The residue was dissolved in ethyl acetate (25 mL), washed with water (2×25 mL) and saturated NaCl. The organic layer was dried over anhydrous Na$_2$SO$_4$, filtered and concentrated. The residue was purified by chromatography (SiO$_2$, 20% ethyl acetate/hexanes) to obtain the title compound (58.7 mg, 0.089 mmol, 99%). $^1$H NMR (CDCl$_3$): 7.65 (d, J=6.9, 1H), 6.68 (d, J=10.2, 1H), 5.96 (m, 1H), 5.42 (d, J=10.2, 1H), 5.06 (m, 2H), 4.01 (m, 2H), 3.21–3.37 (m, 3H), 3.02 (d, J=5.4, 1H), 2.89–2.92 (m, 1H), 2.77–2.85 (m, 1H), 2.57–2.66 (m, 1H), 2.33 (dd, J=14.4, 4.2, 1H), 2.17 (d, J=9.9, 1H), 2.00–2.09 (m, 3H), 1.82 (d, J=1.2, 3H), 1.79 (s, 3H), 1.74 (s, 3H), 1.65 (d, J=0.9, 3H), 1.63 (s, 3H), 1.55 (s, 3H), 1.54 (s, 3H), 1.43 (s, 3H), 1.09 (t, J=7.2, 3H). MS: [M−H]$^-$=658.

EXAMPLE 49

Ethyl 9,10,12-Trihydro-12-hydroxy-gambogate

The target compound was prepared using the method described in Example 48 by running the reaction at −20° C. and using excess of NaBH$_4$ (5×10 mg, followed by 4×5 mg). The crude product was purified by chromatography (SiO$_2$, 20–25% ethyl acetate/hexanes) to give the title compound (34.1 mg, 0.052 mmol, 55%). $^1$H NMR (CDCl$_3$): 6.61 (d, J=10.2, 1H), 6.06 (m, 1H), 5.39 (d, J=10.2, 1H), 5.14 (t, J=7.5, 1H), 5.05 (t, J=6.9, 1H), 4.02 (m, 2H), 3.46 (d, J=5.1, 1H), 3.38–3.34 (m, 2H), 3.64–3.16 (m, 2H), 2.73–2.81 (m, 1H), 2.55–2.62 (m, 1H), 2.39 (d, J=9.3, 1H), 2.15–2.31 (m, 2H), 1.86–2.01 (m, 2H), 1.79 (s, 3H), 1.73 (s, 6H), 1.65 (s, 6H), 1.55 (s, 3H), 1.50 (s, 3H), 1.44 (s, 3H), 1.25 (m, 1H), 1.19 (t, J=7.2, 2H). MS: [M−H]$^-$=660, [M+H]$^+$=662.

EXAMPLE 50

Ethyl 3,4,9,10,27,28,32,33,37,38-Decahydro-10-morpholinyl-gambogate

A solution of ethyl 9,10-dihydro-10-morpholinyl-gambogate (38 mg, 0.051 mmol) in ethyl acetate/ethanol (1:1, 8 mL) and about 50 uL of about 1N HCl was hydrogenated over Pd on carbon at 60 PSI $H_2$ for 2 days. The solvents were removed under vacuum and the residue was purified by chromatography ($SiO_2$, 20% ethyl acetate/hexanes) to give the title compound (29 mg, 0.039 mmol, 75%). 1H NMR ($CDCl_3$): 4.11 (m, 2H), 3.60 (m, 4H), 3.31 (m, 1H), 3.13 (m, 1H), 2.75 (m, 1H), 2.50–2.65 (m, 7H), 2.38–2.43 (m, 3H), 1.76–2.20 (m, 7H), 1.39–1.68 (m, 8H), 2.21–1.34 (m, 13H), 1.19 (d, J=6.6, 3H), 1.11 (s, 3H), 0.94 (d, J=6.6, 6H), 0.88 (d, J=6.6, 6H). MS: $[M-H]^-$=751, $[M+H]^+$=753.

EXAMPLE 51

Ethyl 3,4,27,28,32,33,37,38-Octahydro-gambogate

The title compound was prepared from ethyl 3,4,9,10,27,28,32,33,37,38-decahydro-10-morpholinyl-gambogate using the method described in Example 47. The crude product was purified by chromatography ($SiO_2$, 12% ethyl acetate/hexanes) to give the title compound in about 63% yield. $^1H$ NMR ($CDCl_3$): 7.51 (d, J=6.9, 1H), 3.96 (m, 2H), 3.44 (m, 1H), 2.54–2.66 (m, 4H), 2.46 (d, J=9.3, 1H), 2.3 (dd, J=13.2, 4.5, 1H), 2.10–2.17 (m, 1H), 1.09–1.81 (m, 31H), 0.88–0.96 (m, 14H).

EXAMPLE 52

Identification of Derivatives of Gambogic Acid as Antineoplastic Compounds That are Caspase Cascade Activators and Apoptosis Inducers Human breast cancer cell lines T-47D and ZR-75-1 were grown according to media component mixtures designated by American Type Culture Collection+10% FCS (Invitrogen Corporation), in a 5% $CO_2$-95% humidity incubator at 37° C. T-47D and ZR-75-1 cells were maintained at a cell density between 30 and 80% confluency and for HL-60 at a cell density of 0.1 to 0.6×$10^6$ cells/ml. Cells were harvested at 600×g and resuspended at 0.65×$10^6$ cells/mL into appropriate media+10% FCS. An aliquot of 45 μl of cells was added to a well of a 96-well microtiter plate containing 5 μl of a 10% DMSO in RPMI-1640 media solution containing 1.6 to 100 μM of gambogic acid or other test compound (0.16 to 10 μM final). An aliquot of 45 μl of cells was added to a well of a 96-well microtiter plate containing 5 μM of a 10% DMSO in RPMI-1640 media solution without test compound as the control sample. The samples were mixed by agitation and then incubated at 37° C. for 24 h in a 5% $CO_2$-95% humidity incubator. After incubation, the samples were removed from the incubator and 50 μl of a solution containing 20 μM of N-(Ac-DEVD)-N'-ethoxycarbonyl-R110 fluorogenic substrate SEQ ID NO:1 (Cytovia, Inc.; U.S. Pat. No. 6,335,429), 20% sucrose (Sigma), 20 mM DTT (Sigma), 200 mM NaCl (Sigma), 40 mM Na PIPES buffer pH 7.2 (Sigma), and 500 μg/mL lysolecithin (Calbiochem) was added. The samples were mixed by agitation and incubated at room temperature. Using a fluorescent plate reader (Model 1420 Wallac Instruments), an initial reading (T=0) was made approximately 1–2 min after addition of the substrate solution, employing excitation at 485 nm and emission at 530 nm, to determine the background fluorescence of the control sample. After approximately 3 h of incubation, the samples were read for fluorescence as above (T=3 h).

Calculation:

The Relative Fluorescence Unit values (RFU) were used to calculate the sample readings as follows:

$RFU_{(T=3h)}$–Control $RFU_{(T=0)}$=Net $RFU_{(T=3h)}$

The activity of caspase cascade activation was determined by the ratio of the net RFU value for derivatives of gambogic acid to that of control samples. The $EC_{50}$ (nM) was determined by a sigmoidal dose-response calculation (Prism 2.0, GraphPad Software Inc.). The caspase activity (Ratio) and potency ($EC_{50}$) are summarized in Table I:

TABLE I

Caspase Activity and Potency

| Example # | T-47D Ratio | T-47D EC50 (nM) | ZR-75-1 Ratio | ZR-75-1 EC50 (nM) |
|---|---|---|---|---|
| 4 | 19 | 1342 | 18 | 3983 |
| 5 | 23 | 846 | 5.3 | 2335 |
| 6 | 17 | 714 | 4.1 | 1448 |
| 7 | 2.2 | 598 | 1.6 | >10000 |
| 9 | 15 | 1959 | 16 | 5213 |
| 10 | 23 | 592 | 7.0 | 1383 |

Thus, derivatives of gambogic acid are identified as potent caspase cascade activators and antineoplastic compounds in this assay.

EXAMPLE 53

Identification of Methyl 9,10-Dihydro-10-morpholinyl-gambogate as a Slow Acting Caspase Cascade Activator and Apoptosis Inducers Methyl 9,10-dihydro-10-morpholinyl-gambogate and gambogic acid were assayed as described in Example 28 in T47D cells. The samples of cells and testing compound were incubated for 5 h and 24 h, respectively. Table II summarizes the caspase activity (Ratio) and potency ($EC_{50}$) of methyl 9,10-dihydro-10-morpholinyl-gambogate (compound B) in the 5 h and 24 h assays, in comparison with that of gambogic acid (compound A).

TABLE II

Caspase Activity and Potency of Methyl 9,10-Dihydro-10-morpholinyl-gambogate (compound B) and Gambogic Acid (compound A) in the 5 h and 24 h Assays in T47D cells

| Compound | 5 h Ratio | 5 h EC50 (nM) | 24 h Ratio | 24 h EC50 (nM) |
|---|---|---|---|---|
| A | 29.5 | 1740 | 12.1 | 700 |
| B | 1.2 | >10000 | 19 | 3800 |

Table II showed that methyl 9,10-dihydro-10-morpholinyl-gambogate (compound B) is not active in the 5 h assay but is active in the 24 h assays. In comparison, gambogic acid (compound A) is active both in the 5 h and 24 h assays. Therefore methyl 9,10-dihydro-10-morpholinyl-gambogate is a slow acting caspase cascade activator and apoptosis inducer. In comparison, gambogic acid is a fast acting apoptosis inducer.

EXAMPLE 54

Conversion of Methyl 9,10-Dihydro-10-morpholinyl-gambogate to Methyl Gambogate in Biological Media A solution of methyl 9,10-dihydro-10-morpholinyl-gambogate in 87.5% RPMI 1640 biological Media (Invitrogen Corporation, Carlsbad, Calif.), 5.6% EtOH, 1.3% DMSO, and 5.6% Cremophor EL at a concentration of 5 mg/ml was stored at 37° C. The solution was tested by HPLC at different time points as indicated in Table III. The amount of methyl 9,10-dihydro-10-morpholinyl-gambogate (compound B) and methyl gambogate (compound C) was measured by integration of the peak area. The HPLC was run in the Beckman System Gold with 32 Karate software under the following conditions:

| | |
|---|---|
| Column: | Alltech Platinum EPS C8, 4.6*100 mm, 3 μm |
| Mobile Phase: | Gradient with acetonitrile/water (contained 0.1% trifluoroacetic acid in both mobile phase) in 26 min |
| Flow rate: | 1 ml/min |
| UV absorption: | 278 nm |

The results were summarized in Table III.

TABLE III

Amount of Methyl 9,10-Dihydro-10-morpholinyl-gambogate (compound B) and Methyl Gambogate (compound C) in Biological Media

| Compound | 0 h | 2 h | 18 h | 48 h | 90 h |
|---|---|---|---|---|---|
| B | 92 | 92 | 72 | 49 | 28 |
| C | 4 | 3 | 26 | 48 | 64 |

Table III showed that methyl 9,10-dihydro-10-morpholinyl-gambogate (compound B) was converted slowly (reversal of Michael addition) to methyl gambogate (compound C) at 37° C. in the RPMI biological media.

EXAMPLE 55

Evaluation of Maximum Tolerated Dose (MTD) of Gambogic Acid and Methyl 9,10-Dihydro-10-morpholinyl-gambogate in Mice For acute toxicity studies, 3 ICR (CD-1) mice were used per each dose group. Animals were given a single bolus injection in the tail vein with approximately 100 μl volume of compound formulation or vehicle formulation. Mice body weights were measured daily along with daily observation for clinical abnormalities. The maximum tolerated dose (MTD) was defined as the dose that results in less than 10% decrease in body weight with no clinical abnormalities. The mice were observed for 5 days after the injection and upon termination of the study, necropsy and gross pathology were performed to assess organ health.

For multiple dose studies, the animals were dosed once a day for 5 days. The animals were observed for up to 7 days after the last dose.

Table IV summarizes the MTD of gambogic acid and methyl 9,10-dihydro-10-morpholinyl-gambogate in mice by I.V. administration.

TABLE IV

MTD of Gambogic Acid (compound A) and Methyl 9,10-Dihydro-10-morpholinyl-gambogate (compound B) in Mice

| Compound | Acute MTD | Multiple Dose MTD |
|---|---|---|
| A | 20 to 40 mg/kg | Once a day, 5 doses: 5 mg/kg |
| B | >100 mg/kg | Once a day, 5 doses: >100 mg/kg |

The results in Table IV indicate that methyl 9,10-dihydro-10morpholinyl-gambogate (compound B) was much better tolerated and had significantly less systemic toxicity than gambogic acid (Compound A). In addition, there was evidence of injection site toxicity, such as tail edema, associated with gambogic acid, that precludes the multiple administration of the drug at higher doses, while the injection site toxicity was substantially reduced with methyl 9,10-dihydro-10-morpholinyl-gambogate. These findings indicated that methyl 9,10-dihydro-10-morpholinyl-gambogate reduces the toxicity systemically as well as at the injection site.

EXAMPLE 56

Pharmacokinetic Studies of Gambogic Acid and Methyl 9,10-Dihydro-10morpholinyl-gambogate in Mice ICR mice were administered a single dose of drug into the tail vein. At each time point, 3 animals were sacrificed and the blood was withdrawn by cardiac puncture. The blood cells were spun down and the plasma was collected and frozen immediately in liquid nitrogen. For sample processing, the plasma was thawed and extraction solvent was added along with an internal standard to assess recoveries. The samples were vortexed followed by centrifugation, and the extraction solution was collected and subjected to LC/MS/MS analysis to identify and quantitate the compound plasma concentration. The levels of compound from the three animals at each time point were averaged and the pharmacokinetic parameters calculated using WinNonLin program. Table V summarized the major PK parameters.

TABLE V

PK Parameters of Gambogic Acid (compound A) and Methyl 9,10-Dihydro-10-morpholinyl-gambogate (compound B) at doses close to their respective MTDs

| Compound | A | B | C |
|---|---|---|---|
| Dose | 5 mg/kg | 50 mg/kg | From dosing of B |
| AUC (0-inf), ng-h/ml Area under the curve | 2,700 | 353,021 | 73,433 |
| CL, L/h/kg Clearance | 1.84 | 0.14 | n.a. |
| Vss, L/kg Vol. of distribution | 2.9 | 2.12 | n.a. |
| T1/2, h Terminal half-life | 4.8 | 27.6 | 16.2 |

Pharmacokinetic (PK) analysis of the plasma levels for the two compounds as summarized in Table V indicated that the total exposure to gambogic acid (AUC of 2,700 ng-hr/ml) was substantially less than methyl 9,10-dihydro-10-morpholinyl-gambogate (AUC of 353,021 ng-hr/ml) even with the difference in dose close to their respective MTD. This indicated that the reduced toxicity of methyl 9,10-dihydro-10-morpholinyl-gambogate was not due to decreased drug exposure. The PK analysis also showed that methyl gambogate (compound C) also was present at high concentration (AUC of 73,433 ng-hr/ml) in the plasma. Therefore, similar to the conversion observed in the biological media as shown in Example 30, the conversion of methyl 9,10-dihydro-10-morpholinyl-gambogate to methyl gambogate also was observed in PK studies in the mice.

EXAMPLE 57

Efficacy Studies of Gambogic Acid and Methyl 9,10-Dihydro-10-morpholinyl-gambogate in Mice CD1 nu/nu mice were used. Viable tumor bits of transplantable human xenografts approximately 50 mg of trocar or cultured human tumor cells (nx106 cells?) were implanted subcutaneously into the flank region of mice and tumors were allowed to grow to the desired average size of 100 mg. The mice were measured for tumor size and those within the accepted tumor range of 75–125 mg, were randomized into control and treatment groups with 8–9 mice per group. Treatment was initiated on these groups which have an average starting tumor size of 100 mg. The control group was injected with the vehicle used to dissolve the drug. Other groups received the drug at the dose and schedule as indicated in Table VI. Injections were I.V. via the tail vein. Tumor measurements were taken every other day along with weights of animals and all animals were observed daily for survival. Tumor size was calculated by the equation of:

$$\text{Tumor volume} = (\text{length} \times \text{width}^2)/2.$$

In efficacy studies with human tumor cells implanted subcutaneously into nu/nu mice, the best efficacy with gambogic acid at doses that were toxic was approximately 20% tumor growth inhibition which was not statistically significant.

Anti-tumor efficacy evaluation of methyl 9,10-dihydro-10-morpholinyl-gambogate, in several human tumor xenograft models, demonstrated tumor growth reduction of 50–70% (statistically significant, p=0.01–0.0005) with no significant body weight loss or abnormal behavioral changes. Table VI summarized the in vivo efficacy results.

TABLE VI

Efficacy of Gambogic Acid (compound A) and Methyl 9,10-Dihydro-10-morpholinyl-gambogate (compound B) in Human Tumor Xenograft Mouse Models

| Compound | A | B | B |
|---|---|---|---|
| Dose | 5 mg/kg, every other day | 50 mg/kg, every day | 75 mg/kg, every day |
| Human tumor designation (cancer type) | ZR75-1 (Breast cancer) | MX-1 (Breast cancer) | SW620 (colorectal cancer) |
| % Tumor reduction | 20% | 60% | 58% |

The data in Table VI indicated that gambogic acid did not produce significant efficacy at its maximal tolerable dose. In comparison, methyl 9,10-dihydro-10-morpholinyl-gambogate, a prodrug had a better profile with both good efficacy and reduced toxicity.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A method of treating or ameliorating a disorder responsive to the induction of apoptosis in an animal suffering therefrom, with reduced side effects at the site of administration and reduced systemic toxicity, comprising administering to a mammal in need of such treatment an effective amount of a compound having one of the Formulae I–II:

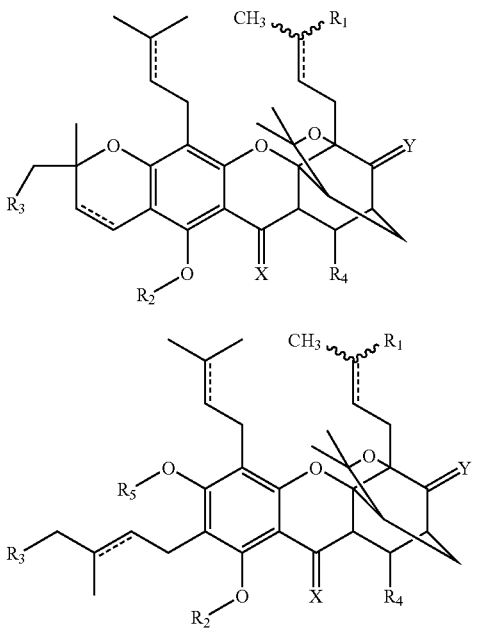

or pharmaceutically acceptable salts or prodrugs thereof, wherein:

the dotted lines are single bonds, double bonds or an epoxy group;

X together with the attached carbon is a methylene, carbonyl, hydroxymethinyl, alkoxymethinyl, aminomethinyl, an oxime, a hydrazone, an arylhydrazone or semicarbazone;

Y together with the attached carbon is a methylene, carbonyl, hydroxymethinyl, alkoxymethinyl, aminomethinyl, an oxime, a hydrazone, an arylhydrazone or semicarbazone;

$R_1$ methylenehydroxy, acyl ($R_a$CO), optionally substituted alkoxycarbonyl ($R_a$OCO), optionally substituted alkylthiocarbonyl, optionally substituted aminocarbonyl (carbamyl, $R_bR_c$NCO) or hydroxyaminocarbonyl, where $R_a$ is optionally substituted lower alkyl, optionally substituted aryl, or optionally substituted lower aralkyl group; $R_b$ and $R_c$ are independently hydrogen, optionally substituted lower alkyl, optionally substituted aryl, or optionally substituted lower aralkyl groups; or $R_b$ and $R_c$ may be taken together with the attached N to form a heterocycle, including piperidine, morpholine and piperazine;

$R_2$ is hydrogen, optionally substituted alkyl, acyl ($R_a$CO), carbamyl ($R_bR_c$NCO) or sulfonyl ($R_d$SO$_2$), where $R_a$, $R_b$ and $R_c$ are defined above; $R_d$ is hydrogen, optionally substituted lower alkyl, optionally substituted aryl, or optionally substituted lower aralkyl groups;

$R_3$ is hydrogen or prenyl;

$R_4$ is alkoxy, arylalkoxy, alkylthio, arylalkylthio, amino, aminoalkoxy, optionally substituted saturated or partially saturated heterocyclo, heterocycloalkoxy or heterocycloalkylamino; and $R_5$ is hydrogen, optionally substituted alkyl or acyl ($R_a$CO), carbamyl ($R_bR_d$NCO) or sulfonyl ($R_d$SO$_2$), where $R_a$, $R_b$, $R_c$ and $R_d$ are defined above; wherein said compound causes no side effects at the site of administration;

wherein said disorder responsive to the induction of apoptosis is inflammation, inflammatory bowel disease, psoriasis, rheumatoid arthritis, multiple sclerosis, diabetes mellitus, Hashimoto's thyroiditis, autoimmune lymphoproliferative syndrome, or a cancer selected from the group consisting of Hodgkin's disease, non-Hodgkin's lymphoma, acute and chronic lymphocytic leukemias, multiple myeloma, neuroblastoma, breast carcinoma, ovarian carcinoma, lung carcinoma, Wilms' tumor, cervical carcinoma, testicular carcinoma, soft-tissue sarcoma, chronic lymphocytic leukemia, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head and neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer and prostatic carcinoma.

2. The method of claim 1, wherein $R_a$ is —(CH$_2$CH$_2$O)$_n$R$_m$ wherein n=1–10 and $R_m$ is hydrogen or C$_{1-10}$ alkyl.

3. The method of claim 2, wherein $R_1$ is 2-hydroxy-ethoxycarbonyl, 2-{2-[2-(2-methoxyethoxy)-ethoxy]ethoxy}ethoxy-carbonyl, 2-[2-(2-ethoxyethoxy)-ethoxy]ethoxycarbonyl, or 2-{2-[2-(2-octyloxyethoxy)ethoxy]ethoxy}ethoxy-carbonyl.

4. The method of claim 1, wherein $R_4$ is 2-dimethylaminoethoxy, morpholinyl, 2-(morpholinyl)ethoxy, 2-(morpholinyl)ethylamino, piperidinyl, piperazinyl, 4-methylpiperazinyl, 4-acetylpiperazinyl or 4-(2-pyridyl)piperazinyl.

5. The method of claim 1, wherein said side effects are tissue damage or cell death at the site of administration.

6. The method of claim 5, wherein said tissue is dermal, vascular, arterial, fatty or muscular tissue.

7. The method of claim 5, wherein said tissue damage is necrosis, burning, irritation, eruption or inflammation.

8. The method of claim 1, wherein said compounds have substantially reduced systemic toxicity.

9. The method of claim 1, wherein said disorder is cancer.

10. The method according to claim 9, wherein said compound is administered together with at least one known cancer chemotherapeutic agent, or a pharmaceutically acceptable salt of said agent.

11. The method of claim 1, wherein said disorder is drug resistant cancer.

12. The method according to claim 1, wherein said compound is administered together with at least one compound selected from the group consisting of busulfan, cisplatin, mitomycin C, carboplatin, colchicine, vinblastine, paclitaxel, docetaxel, camptothecin, topotecan, doxorubicin, etoposide, 5-azacytidine, 5-fluorouracil, methotrexate, 5-fluoro-2'-deoxy-uridine, ara-C, hydroxyurea, thioguanine, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, Herceptin®, Rituxan®, arsenic trioxide, gamcitabine, doxazosin, terazosin, tamsulosin, CB-64D, CB-184, haloperidol, lovastatin, simvastatin, pravastatin, fluvastatin, atorvastatin, cerivastatin, amprenavir, abacavir, CGP-73547, CGP-61755, DMP-450 indinavir, nelfinavir, tipranavir, ritonavir, saquinavir, ABT-378, AG 1776, BMS- 232,632, bexarotene, tretinoin, 13-cis-retinoic acid, 9-cis-retinoic acid, α-difluoromethylornithine, ILX23-7553, fenretinide, N-4-carboxyphenyl retinamide, lactacystin, MG-132, PS-341, Gleevec®, ZD1839 (Iressa®), SH268, genistein, CEP2563, SU6668, SU11248, EMD121974, R115777, SCH66336, L-778,123, BAL9611, TAN-1813, flavopiridol, UCN-01, roscovitine, olomoucine, celecoxib, valecoxib, rofecoxib and alanosine.

13. The method according to claim 12, wherein said compound(s) are administered after surgical treatment for cancer.

14. The method according to claim 9 or 11, wherein said animal is also treated with radiation therapy.

15. The method according to claim 1, wherein said disorder is an autoimmune disease.

16. The method according to claim 1, wherein said disorder is an infectious viral disease.

17. The method according to claim 1, wherein said disorder is rheumatoid arthritis.

18. The method according to claim 1, wherein said disorder is an inflammatory disease.

19. The method according to claim 1, wherein said disorder is psoriasis.

20. The method according to claim 1, wherein said disorder is a skin disease.

21. The method of claim 1, wherein said compound is selected from the group consisting of:
   9,10-Dihydro-10-[4-(2-pyridyl)piperazinyl]-gambogyl (N-methylpiperazine);
   9,10-Dihydro-10-[2-(morpholinyl)ethoxy]-gambogyl (N-methylpiperazine);
   9,10-Dihydro-10-(2-dimethylaminoethoxy)-gambogyl (N-methylpiperazine);
   9,10-Dihydro-10-ethoxy-gambogyl piperidine;
   Ethyl 9,10-dihydro-10-morpholinyl-gambogate;
   Methyl 9,10-dihydro-10-benzyloxy-gambogate;
   Methyl 9,10-dihydro-10-(4-acetylpiperazinyl)-gambogate;
   Methyl 9,10-dihydro-10-(piperidinyl)-gambogate;
   9,10-Dihydro-10-[4-(2-pyridyl)piperazinyl]-gambogyl (diethylamine);
   9,10-Dihydro-10-[4-(2-pyridyl)piperazinyl]-gambogyl (methylamine);
   9,10-Dihydro-10-(morpholinyl)-gambogyl (diethylamine);
   9,10-Dihydro-10-ethoxy-gambogyl (diethylamine);
   Ethyl 9,10-dihydro-10-ethoxy-gambogate;
   Methyl 9,10-dihydro-10-(4-methylpiperazinyl)-gambogate;
   Ethyl 9,10-dihydro-10-(piperidinyl)-gambogate;
   Ethyl 9,10-dihydro-10-(4-methylpiperazinyl)-gambogate; and
   Ethyl 9,10-dihydro-10-(4-acetylpiperazinyl)-gambogate.

22. The method of claim 1, wherein said compound is selected from the group consisting of:
   9,10-Dihydro-10-morpholinyl-gambogyl piperidine;
   9,10-Dihydro-10-piperidinyl-gambogyl piperidine;
   Methyl 9,10-dihydro-10-morpholinyl-gambogate.
   9,10-Dihydro-10-(4-(2-pyridyl)piperazinyl)gambogyl-(4-(2-pyridyl)-piperazine); and
   9,10-Dihydro-10-methoxy-gambogyl piperidine.

23. The method of claim 1, wherein said compound is selected from the group consisting of:
   2-{2-[2-(2-Octyloxyethoxy)ethoxy]ethoxy}ethyl 9,10-Dihydro-10-morpholinyl gambogate;
   2-[2-(2-Ethoxyethoxy)ethoxy]ethyl 9,10-Dihydro-10-morpholinyl gambogate;
   Propyl 9,10-Dihydro-10-morpholinyl-gambogate;
   2-{2-[2-(2-Methoxyethoxy)ethoxy]ethoxy}ethyl 9,10-Dihydro-10-morpholinyl-gambogate;
   2-Hydroxyethyl 9,10-Dihydro-10-morpholinyl-gambogate;
   Butyl 9,10-Dihydro-10-morpholinyl-gambogate;
   Isobutyl 9,10-Dihydro-10-morpholinyl-gambogate;
   Ethyl 3,4,9,10,32,33,37,38-Octahydro-10-morpholinyl-gambogate; and
   Ethyl 3,4,9,10,27,28,32,33,37,38-Decahydro-10-morpholinyl-gambogate.

24. The method of claim 1, wherein said compound is administered as part of an intravenous dosage form comprising an effective amount of said compound and a pharmaceutically acceptable formulation.

25. The method of claim 1, wherein said effective amount is in the range of 0.01 mg/kg to 200 mg/kg.

26. A method of treating or ameliorating a disorder responsive to the induction of apoptosis in an animal suffering therefrom, comprising administering to a mammal in need of such treatment an effective amount of a compound selected from the group consisting of:
   9,10-Dihydro-10-morpholinyl-gambogyl (N-methylpiperazine);
   9,10-Dihydro-10-piperidinyl-gambogyl (N-methylpiperazine);
   9,10-Dihydro-10-[2-(morpholinyl)ethylamino]-gambogyl (N-methylpiperazine);
   9,10-Dihydro-10-[4-(2-pyridyl)piperazinyl]-gambogyl (N-methylpiperazine);
   9,10-Dihydro-10-[2-(morpholinyl)ethoxy]-gambogyl (N-methylpiperazine);
   9,10-Dihydro-10-(2-dimethylaminoethoxy)-gambogyl (N-methylpiperazine);
   9,10-Dihydro-10-ethoxy-gambogyl piperidine
   9,10-Dihydro-10-morpholinyl-gambogyl (dimethylamine);
   Ethyl 9,10-dihydro-10-morpholinyl-gambogate;
   Methyl 9,10-dihydro-10-benzyloxy-gambogate;
   Methyl 9,10-dihydro-10-(4-acetylpiperazinyl)-gambogate;
   Methyl 9,10-dihydro-10-(piperidinyl)-gambogate;
   9,10-Dihydro-10-[4-(2-pyridyl)piperazinyl]-gambogyl (diethylamine);
   9,10-Dihydro-10-[4-(2-pyridyl)piperazinyl]-gambogyl (methylamine);
   9,10-Dihydro-10-(morpholinyl)-gambogyl (diethylamine);
   Methyl 9,10-dihydro-10-ethoxy-gambogate;
   9,10-Dihydro-10-ethoxy-gambogic acid;
   9,10-Dihydro-10-ethoxy-gambogyl (diethylamine);
   Ethyl 9,10-dihydro-10-ethoxy-gambogate;
   Methyl 9,10-dihydro-10-(4-methylpiperazinyl)-gambogate;
   Ethyl 9,10-dihydro-10-(piperidinyl)-gambogate;
   Ethyl 9,10-dihydro-10-(4-methylpiperazinyl)-gambogate; and
   Ethyl 9,10-dihydro-10-(4-acetylpiperazinyl)-gambogate,
   Ethyl gambogate; and
   Gambogyl methylamine;
   wherein said disorder responsive to the induction of apoptosis is inflammation, inflammatory bowel disease, psoriasis, rheumatoid arthritis, multiple sclerosis, diabetes mellitus, Hashimoto's thyroiditis, autoimmune lymphoproliferative syndrome, or a cancer selected from the group consisting of Hodgkin's disease, non-Hodgkin's lymphoma, acute and chronic lymphocytic leukemias, multiple myeloma, neuroblastoma, breast carcinoma, ovarian carcinoma, lung carcinoma, Wilms' tumor, cervical carcinoma, testicular carcinoma, soft-tissue sarcoma, chronic lymphocytic leukemia, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head and neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer and prostatic carcinoma.

27. The method of claim 26, wherein said compound is selected from the group consisting of:
2-{2-[2-(2-Octyloxyethoxy)ethoxy]ethoxy}ethyl Gambogate;
2-{2-[2-(2-Octyloxyethoxy)ethoxy]ethoxy}ethyl-9,10-Dihydro-10-morpholinyl gambogate;
2-[2-(2-Ethoxyethoxy)ethoxy]ethyl Gambogate;
2-[2-(2-Ethoxyethoxy)ethoxy]ethyl-9,10-Dihydro-10-morpholinyl gambogate;
Propyl gambogate;
Propyl 9,10-Dihydro-10-morpholinyl-gambogate;
2-{2-[2-(2-Methoxyethoxy)ethoxy]ethoxy}ethyl gambogate;
2-{2-[2-(2-Methoxyethoxy)ethoxy]ethoxy}ethyl-9,10-Dihydro-10-morpholinyl-gambogate;
2-Hydroxyethyl gambogate;
2-Hydroxyethyl 9,10-Dihydro-10-morpholinyl-gambogate;
Methyl 9,10-Dihydro-gambogate and Methyl 9,10,12-Trihydro-12-hydroxy-gambogate;
Methyl 32,33-Epoxy-37,38-epoxy-gambogate;
Methyl 37,38-Epoxy gambogate;
Methyl 9,10-Epoxy-gambogate;
Butyl gambogate;
Isobutyl gambogate;
Butyl 9,10-Dihydro-10-morpholinyl-gambogate;
Isobutyl 9,10-Dihydro-10-morpholinyl-gambogate;
Ethyl 12-hydro-12-hydroxy-gambogate;
Ethyl 3,4,32,33,37,38-hexahydro-gambogate;
Ethyl 3,4,27,28,32,33,37,38-octahydro-gambogate
Ethyl 3,4,9,10,32,33,37,38-Octahydro-10-morpholinyl-gambogate; and
Ethyl 3,4,9,10,27,28,32,33,37,38-Decahydro-10-morpholinyl-gambogate.

28. The method of claim 27, wherein said disorder is cancer.

29. The method of claim 27, wherein said disorder is drug resistant cancer.

30. The method according to claim 28 or 29, wherein said compound is administered together with at least one known cancer chemotherapeutic agent, or a pharmaceutically acceptable salt of said agent.

31. The method according to claim 30, wherein said compound is administered together with at least one compound selected from the group consisting of busulfan, cisplatin, mitomycin C, carboplatin, colchicine, vinblastine, paclitaxel, docetaxel, camptothecin, topotecan, doxorubicin, etoposide, 5-azacytidine, 5-fluorouracil, methotrexate, 5-fluoro-2'-deoxy-uridine, ara-C, hydroxyurea, thioguanine, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, Herceptin®, Rituxan®, arsenic trioxide, gamcitabine, doxazosin, terazosin, tamsulosin, CB-64D, CB-184, haloperidol, lovastatin, simvastatin, pravastatin, fluvastatin, atorvastatin, cerivastatin, amprenavir, abacavir, CGP-73547, CGP-61755, DMP-450, indinavir, nelfinavir, tipranavir, ritonavir, saquinavir, ABT-378, AG 1776, BMS-232,632, bexarotene, tretinoin, 13-cis-retinoic acid, 9-cis-retinoic acid, α-difluoromethylornithine, ILX23-7553, fenretinide, N-4-carboxyphenyl retinamide, lactacystin, MG-132, PS-341, Gleevec®, ZD1839 (Iressa®), SH268, genistein, CEP2563, SU6668, SU11248, EMD121974, R115777, SCH66336, L-778,123, BAL9611, TAN-1813, flavopiridol, UCN-01, roscovitine, olomoucine, celecoxib, valecoxib, rofecoxib and alanosine.

32. The method according to claim 28 or 29, wherein said animal is also treated with radiation therapy.

33. The method according to claim 28 or 29, wherein said compound(s) are administered after surgical treatment for cancer.

34. The method according to claim 27, wherein said disorder is an autoimmune disease.

35. The method according to claim 27, wherein said disorder is an infectious viral disease.

36. The method according to claim 27, wherein said disorder is rheumatoid arthritis.

37. The method according to claim 27, wherein said disorder is an inflammatory disease.

38. The method according to claim 27, wherein said disorder is psoriasis.

39. The method according to claim 27, wherein said disorder is a skin disease.

40. A compound selected from the group consisting of:
9,10-Dihydro-10-morpholinyl-gambogyl (N-methylpiperazine);
9,10-Dihydro-10-piperidinyl-gambogyl (N-methylpiperazine);
9,10-Dihydro-10-[2-(morpholinyl)ethylamino]-gambogyl (N-methylpiperazine);
9,10-Dihydro-10-[4-(2-pyridyl)piperazinyl]-gambogyl (N-methylpiperazine);
9,10-Dihydro-10-[2-(morpholinyl)ethoxy]-gambogyl (N-methylpiperazine);
9,10-Dihydro-10-(2-dimethylaminoethoxy)-gambogyl (N-methylpiperazine);
9,10-Dihydro-10-ethoxy-gambogyl piperidine;
9,10-Dihydro-10-morpholinyl-gambogyl (dimethylamine);
Ethyl 9,10-dihydro-10-morpholinyl-gambogate;
Methyl 9,10-dihydro-10-benzyloxy-gambogate;
Methyl 9,10-dihydro-10-(4-acetylpiperazinyl)-gambogate;
Methyl 9,10-dihydro-10-(piperidinyl)-gambogate;
9,10-Dihydro-10-[4-(2-pyridyl)piperazinyl]-gambogyl (diethylamine);
9,10-Dihydro-10-[4-(2-pyridyl)piperazinyl]-gambogyl (methylamine);
9,10-Dihydro-10-(morpholinyl)-gambogyl (diethylamine);
Methyl 9,10-dihydro-10-ethoxy-gambogate;
9,10-Dihydro-10-ethoxy-gambogic acid;
9,10-Dihydro-10-ethoxy-gambogyl (diethylamine);
Ethyl 9,10-dihydro-10-ethoxy-gambogate;
Methyl 9,10-dihydro-10-(4-methylpiperazinyl)-gambogate;

Ethyl 9,10-dihydro-10-(piperidinyl)-gambogate;
Ethyl 9,10-dihydro-10-(4-methylpiperazinyl)-gambogate; and
Ethyl 9,10-dihydro-10-(4-acetylpiperazinyl)-gambogate;
Ethyl gambogate; and
Gambogyl methylamine.

41. A compound selected from the group consisting of:
2-{2-[2-(2-Octyloxyethoxy)ethoxy]ethoxy}ethyl Gambogate;
2-{2-[2-(2-Octyloxyethoxy)ethoxy]ethoxy}ethyl 9,10-Dihydro-10-morpholinyl gambogate;
2-[2-(2-Ethoxyethoxy)ethoxy]ethyl Gambogate;
2-[2-(2-Ethoxyethoxy)ethoxy]ethyl 9,10-Dihydro-10-morpholinyl gambogate;
Propyl Gambogate;
Propyl 9,10-Dihydro-10-morpholinyl-gambogate;
2-{2-[2-(2-Methoxyethoxy)ethoxy]ethoxy}ethyl gambogate;
2-{2-[2-(2-Methoxyethoxy)ethoxy]ethoxy}ethyl 9,10-Dihydro-10-morpholinyl-gambogate;
2-Hydroxyethyl Gambogate;
2-Hydroxyethyl 9,10-Dihydro-10-morpholinyl-gambogate;
Methyl 9,10-Dihydro-gambogate and Methyl 9,10,12-Trihydro-12-hydroxy-gambogate;
Methyl 32,33-Epoxy-37,38-epoxy-gambogate and Methyl 37,38-Epoxy gambogate;
Methyl 9,10-Epoxy-gambogate;
Butyl Gambogate;
Isobutyl Gambogate;
Butyl 9,10-Dihydro-10-morpholinyl-gambogate;
Isobutyl 9,10-Dihydro-10-morpholinyl-gambogate;
3,4,9,10,32,33,37,38-Octahydro-gambogic Acid;
Ethyl 3,4,9,10,32,33,37,38-Octahydro-10-morpholinyl-gambogate;
Ethyl 3,4,32,33,37,38-Hexahydro-gambogate;
Ethyl 12-Hydro-12-hydroxy-gambogate;
Ethyl 9,10,12-Trihydro-12-hydroxy-gambogate;
Ethyl 3,4,9,10,27,28,32,33,37,38-Decahydro-10-morpholinyl-gambogate; and
Ethyl 3,4,27,28,32,33,37,38-Octahydro-gambogate.

42. A pharmaceutical composition, comprising a compound of claim 40 or 41 and a pharmaceutically acceptable carrier.

43. The pharmaceutical composition of claim 42, further comprising at least one known cancer chemotherapeutic agent, or a pharmaceutically acceptable salt of said agent.

44. The pharmaceutical composition of claim 42, wherein said compound is administered together with at least one compound selected from the group consisting of busulfan, cis-platin, mitomycin C, carboplatin, colchicine, vinblastine, paclitaxel, docetaxel, camptothecin, topotecan, doxorubicin, etoposide, 5-azacytidine, 5-fluorouracil, methotrexate, 5-fluoro-2'-deoxy-uridine, ara-C, hydroxyurea, thioguanine, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, Herceptin®, Rituxan®, arsenic trioxide, gamcitabine, doxazosin, terazosin, tamsulosin, CB-64D, CB-184, haloperidol, lovastatin, simvastatin, pravastatin, fluvastatin, atorvastatin, cerivastatin, amprenavir, abacavir, CGP-73547, CGP-61755, DMP-450, indinavir, nelfinavir, tipranavir, ritonavir, saquinavir, ABT-378, AG 1776, BMS-232,632, bexarotene, tretinoin, 13-cis-retinoic acid, 9-cis-retinoic acid, α-difluoromethylornithine, ILX23-7553, fenretinide, N-4-carboxyphenyl retinamide, lactacystin, MG-132, PS-341, Gleevec®, ZD1839 (Iressa®), SH268, genistein, CEP2563, SU6668, SU11248, EMD121974, R115777, SCH66336, L-778,123, BAL9611, TAN-1813, flavopiridol, UCN-01, roscovitine, olomoucine, celecoxib, valecoxib, rofecoxib and alanosine.

45. The method of claim 27, wherein said compound is Methyl 9,10-Epoxy-gambogate.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: N-terminal acetyl
<220> FEATURE:
<221> NAME/KEY: MOD_RES
<222> LOCATION: (4)..(4)
<223> OTHER INFORMATION: C-terminal N'-ethoxycarbonyl-Rhodamine 110

<400> SEQUENCE: 1

Asp Glu Val Asp
1
```